(12) United States Patent
Santerre et al.

(10) Patent No.: US 10,973,950 B2
(45) Date of Patent: Apr. 13, 2021

(54) BIOMATERIAL WITH REDUCED INFLAMMATORY RESPONSE

(71) Applicant: THE GOVERNING COUNCIL OF THE UNIVERSITY OF TORONTO, Toronto (CA)

(72) Inventors: Paul Santerre, Toronto (CA); Kyle Battiston, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 0 days.

(21) Appl. No.: 15/503,861

(22) PCT Filed: Aug. 14, 2015

(86) PCT No.: PCT/CA2015/000461
§ 371 (c)(1),
(2) Date: Feb. 14, 2017

(87) PCT Pub. No.: WO2016/023102
PCT Pub. Date: Feb. 18, 2016

(65) Prior Publication Data
US 2017/0232142 A1 Aug. 17, 2017

Related U.S. Application Data

(60) Provisional application No. 62/037,359, filed on Aug. 14, 2014.

(51) Int. Cl.
| | |
|---|---|
| A61L 27/16 | (2006.01) |
| C08F 220/06 | (2006.01) |
| C08F 220/18 | (2006.01) |
| A61L 27/54 | (2006.01) |
| A61K 47/32 | (2006.01) |
| A61L 27/14 | (2006.01) |

(Continued)

(52) U.S. Cl.
CPC .............. *A61L 27/16* (2013.01); *A61K 47/32* (2013.01); *A61L 27/14* (2013.01); *A61L 27/18* (2013.01); *A61L 27/34* (2013.01); *A61L 27/54* (2013.01); *A61L 31/06* (2013.01); *A61L 31/10* (2013.01); *A61L 31/16* (2013.01); *C08F 220/06* (2013.01); *C08F 220/18* (2013.01); *C08F 283/008* (2013.01); *A61L 2400/18* (2013.01)

(58) Field of Classification Search
None
See application file for complete search history.

(56) References Cited

U.S. PATENT DOCUMENTS

2002/0133072 A1* 9/2002 Wang ................... A61L 29/085
600/423

OTHER PUBLICATIONS

Sharifpoor, S., et al., Synthesis and Characterization of Degradable Polar Hydrophobic Ionic Polyurethane Scaffolds for Vascular Tissue Engineering Applications, Biomacromolecules, 10 (2009) pp. 2729-2739. (Year: 2009).*

(Continued)

*Primary Examiner* — Dominic Lazaro
(74) *Attorney, Agent, or Firm* — Norton Rose Fulbright US LLP

(57) ABSTRACT

Polar hydrophobic ionic materials and, in particular, polar hydrophobic ionic polyurethanes having a minimum ratio of hydrophobic and anionic components to the remainder of the polymer components are provided that exhibit reduced IgG Fab exposure.

23 Claims, 14 Drawing Sheets

Figure 1:
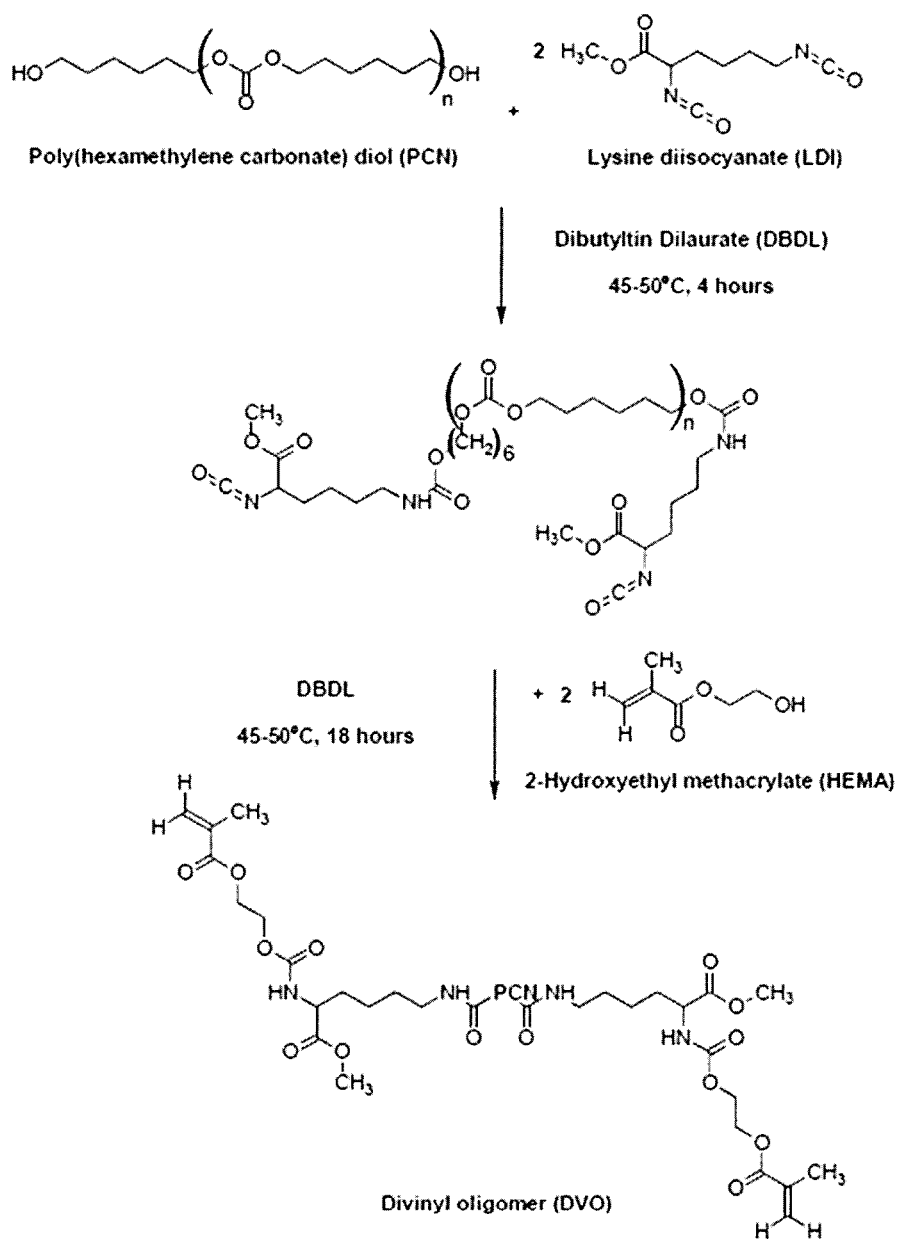
Figure 1:
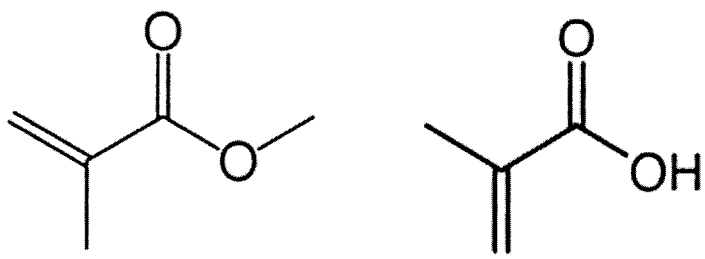

(51) Int. Cl.
- A61L 27/34 (2006.01)
- A61L 31/06 (2006.01)
- A61L 27/18 (2006.01)
- A61L 31/16 (2006.01)
- C08F 283/00 (2006.01)
- A61L 31/10 (2006.01)

(56) References Cited

OTHER PUBLICATIONS

Bastian et al., "IgG deposition and activation of the classical complement pathway involvement in the activation of human granulocytes by decellularized porcine heart valve tissue," *Biomaterials*, 2008; 29: 1824-1832.

Battiston et al., "Effect of polar, hydrophobic, and ionic polyurethane character on adsorbed IgG-mediated monocyte activation," $31^{st}$ Annual Meeting of the Canadian Biomaterials Society, Halifax, Nova Scotia, Jun. 4-7, 2014, Abstract 113486.

Battiston et al., "Immunomodulatory polymeric scaffold enhances extracellular matrix production in cell co-cultures under dynamic mechanical stimulation," *Acta Biomaterialia*, 2015; 24:74-86.

Battiston et al., "Interaction of a block-co-polymeric biomaterial with immunoglobulin G. modulates human monocytes towards a non-inflammatory phenotype," *Acta Biomaterialia*, 2015; 24: 35-43.

Battiston et al., "Monocyte/macrophage cytokine activity regulates vascular smooth muscle cell function within a degradable polyurethane scaffold," *Acta Biomaterialia*, 2014; 10: 1143-1155.

Battiston et al., "Protein binding mediation of biomaterial-dependent monocyte activation on a degradable polar hydrophobic ionic polyurethane," *Biomaterials*, 2012; 33: 8316-8328.

Battiston, Kyle Giovanni, "Evaluating the Use of Monocytes with a Degradable Polyurethane for Vascular Tissue Regeneration," PhD Thesis, University of Toronto, 2015, 1-322.

Benahmed et al., "Biodegradation of synthetic biphasic calcium phosphate by human monocytes in vitro: a morphological study," *Biomaterials*, 1996; 17: 2173-2178.

Bouafsoun et al., "Evaluation of Endothelial Cell Adhesion onto Different Protein/Gold Electrodes by EIS," *Macromol. Biosci.*, 2007; 7: 599-610.

Carillo-Conde et al., "Chemistry-dependent adsorption of serum proteins onto polyanhydride microparticles differentially influences dendritic cell uptake and activation," *Acta Biomaterialia*, 2012; 8(10): 3618-3628.

Cheung et al., "Pro-Angiogenic Character of Endothelial Cells and Gingival Fibroblasts Cocultures in Perfused Degradable Polyurethane Scaffolds," *Tissue Engineering: Part A*, 2015; 21(9-10): 1587-1599.

De Paoli et al., "The effect of protein corona composition on the interaction of carbon nanotubes with human blood platelets," *Biomaterials*, 2014; 35: 6182-6194.

DiFazio et al., "Multiple Platelet Surface Receptors Mediate Platelet Adhesion to Surfaces Coated with Plasma Proteins," *Journal of Surgical Research*, 1994; 57(1):133-137.

Haralick, Robert M. and Linda G. Shapiro, *Computer and Robot Vision*, Addison-Wesley Longman, 1992.

Jenney, Christopher R. and James M. Anderson, "Adsorbed IgG: a potent adhesive substrate for human macrophages," Student Research Award in the Ph.D. Degree Candidate Category, World Biomaterials Congress 2000, Kamuela, HI, May 15-20, 2000, John Wiley and Sons, 2000, 281-290.

Mathieu et al., "Characterization of a degradable polar hydrophobic ionic polyurethane with circulating angiogenic cells in vitro," *Journal of Biomaterials Science, Polymer Edition*, 2014; 25(11): 1159-1173.

McBane et al., "Biodegradation and in vivo biocompatibility of a degradable polar/hydrophobic/ionic polyurethane for tissue engineering applications," *Biomaterials*, 2011; 32: 6034-6044.

Okagaki et al., "Measurement of Number and Cross-Sectional Area of Basal Cell Psuedopodia: A New Morphometric Method," *Journal of Cell Biology*, 1981; 91: 629-636.

Ross, Jacqui, "ImageJ: Introduction to Image Analysis," *Biomedical Imaging Research Unit, School of Medical Sciences*, University of Auckland, 2012.

Schmidt et al., "Fetal bovine serum xenoproteins modulate human monocyte adhesion and protein release on biomaterials in vitro," *Acta Biomater*. 2011; 7(2): 515-525.

Sharifpoor et al., "Influence of Degradable Polar Hydrophobic Ionic Polyurethanes and Cyclic Mechanical Strain on Vascular Smooth Muscle Cell Function and Phenotype," *Institute of Biomaterials and Biomedical Engineering*, University of Toronto, 2011. 1-269.

Sharifpoor.et al., "Synthesis and Characterization of Degradable Polar Hydrophobic Ionic Polyurethane Scaffolds for Vascular Tissue Engineering Applications," *Biomacromolecules*, 2009; 10: 2729-2739.

Shen et al., "Effects of adsorbed proteins and surface chemistry on foreign body giant cell formation, tumor necrosis factor alpha release and procoagulant activity of monocytes," *Journal of Biomedical Materials Research, Part A*, 2004; 70A(4): 533-541.

Sinko, Patrick J. and Yashveer Singh eds., *Martin's Physical Pharmacy and Pharmaceutical Sciences: Physica Chemical and Biopharmaceutical Sciences*, 6th ed. Lippincott Williams & Wilkins: New York, 2011.

Tang et al., "Inflammatory responses to implanted polymeric biomaterials: Role of surface-adsorbed immunoglobulin G," *J. Lab. Clin. Med.*, 1993; 122(3): 292-300.

Wettero et al., "Complement activation on immunoglobulin G-coated hydrophobic surfaces enhances the release of oxygen radicals from neutrophils through an actin-dependent mechanism," *Journal of Biomedical Materials Research*, 2000; 51(4): 742-751.

Young et al., "Human monocyte adhesion and activation on crystalline polymers with different morphology and wettability in vitro" *Journal of Biomedical Materials Research, Part A*, 2000; 50(4): 490-498.

International Search Report and Written Opinion issued in Application No. PCT/CA2015/000461, dated Nov. 19, 2015.

European Search Report Issued in Corresponding European Patent Application No. 15832031, dated Mar. 15, 2018.

McDonald, "Characterization of a Degradable Polar Hydrophobic Ionic Polyurethane Using a Monocyte/Endothelial Cell Co-Culture (In Vitro) and a Subcutaneous Implant Mouse Model (In Vivo)," Thesis, Ottawa, Canada 2011.

\* cited by examiner

BIOMATERIAL WITH REDUCED INFLAMMATORY RESPONSE

CROSS-REFERENCE TO RELATED APPLICATIONS

This application is a national phase application under 35 U.S.C. § 371 of International Application No. PCT/CA2015/000461 filed 14 Aug. 2015, which claims priority to U.S. Provisional Application No. 62/037,359 filed 14 Aug. 2014. The entire contents of each of the abovereferenced disclosures is specifically incorporated by reference herein without disclaimer.

TECHNICAL FIELD

This patent application relates to biocompatible biomaterials.

BACKGROUND OF THE ART

The immune system represents the body's defense mechanism against invasion by antigens or non-self entities, including foreign materials, pathogens, and other infectious agents. In vertebrates, two types of immune responses exist—innate immunity and adaptive immunity. The innate immune response is comprised of physical and chemical barriers that prevent the entry of foreign antigens in a nonspecific manner and immune cells that recognize a limited number of receptors possessed by a variety of pathogens. In contrast, the adaptive immune system, which involves unique recognition and a more tailored cellular response, demonstrates a greater specificity towards the invading antigen.

Inflammation is a fundamental reaction involved in the innate immune response and manifests itself through the classical symptoms of redness, pain, heat, and swelling. The inflammatory response is initiated by physical injury or infection and represents one of the first responses of the body's immune system to the aforementioned events. The inflammatory response is characterized by the activation and migration of leukocytes to the injury site during acute inflammation and the presence of mononuclear cells during chronic inflammation; the subsequent cascade of cellular processes is the body's attempt to identify, contain, and eliminate foreign materials and pathogens that may be present. This system aims to repair or restore the structure and function of the injured tissue or organ, thereby contributing to the wound-healing response and maintaining the well-being of the organism as a whole.

Physical injury occurs when a biomedical device is implanted into the body. Once implanted, it is recognized by the immune system as a foreign entity. The resulting injury and interaction of the biomaterial with the body triggers the inflammatory response. The initial sequence of events appears similar to, but ultimately diverges from, the process of normal wound healing. A series of immunological events collectively described as the foreign body reaction (FBR) follow implantation and may result in fibrotic encapsulation of the biodevice. Fibrotic encapsulation may interfere with device functionality or render the device useless or result in secondary complications such as painful adhesions, inability of blood cells to gain access to tissue in order to fight infections and provide nutrients to cells, and build up of body fluids around the implant. The outcome of the FBR determines the host response to the biomedical device, which affects its acceptance or rejection by the body. Several phases are encountered during the host response to the biomaterial, including blood-material interaction, acute inflammation, chronic inflammation, FBR, and fibrosis, in which specific cell populations are present during each phase.

Biomaterials are used in numerous biomedical applications and devices, such as heart valves, biosensors, tissue engineering scaffolds and joint replacements just to name a few, both in vivo as an implant for short or long times, and in vitro in contact with cells and/or tissues, and/or body fluids such as in blood fields and analytical biosensors. Protein adsorption occurs immediately following the implantation of a biomaterial, or contact of body fluids such as blood to a biomaterial. This adsorbed protein layer is composed of bioactive agents that can greatly influence the behavior of cells or other body fluid elements (platelets, proteins, red blood cells, neutrophils etc.) involved in the inflammatory, immune, and foreign body responses such as wound-healing responses. The adsorbed protein layer initiates the coordinated series of innate immunological events collectively described as FBR.

There remains a need for materials that are biocompatible and provide a more desirable immune response and/or a more controllable immune response than commonly used biomaterials.

BRIEF SUMMARY

In one aspect, there is provided a synthetic biocompatible polymer material comprising the reaction product of: (a) at least one polar non-ionic macromer component; one or both of: (b) at least one anionic component; and (c) at least one hydrophobic component; wherein the molar ratio of (a) to (b) and (c) combined is at least about 1:10 (i.e. (b)+(c) is greater than (a)); wherein the molar ratio of (b) to (c) is between about 20:1 and 1:100; and wherein the maximum combined number of different types of monomer components (a), (b) and (c) in the polymer is 9. In one embodiment, the molar ratio of (a) to (b) and (c) is at least about 1:20. In one embodiment, the molar ratio of (a) to (b) and (c) is at least about 1:>20.

The maximum number of monomers comprising the synthetic polymer material is 9. Accordingly, the number of monomers comprising (a) may be 8 (where (b) or (c) is absent), 7, 6, 5, 4, 3, 2, or 1. The number of monomers comprising (b) may be 8 (where (c) is absent), 7, 6, 4, 3, 2, 1 or 0. The number of monomers comprising (c) may be 8 (where (b) is absent), 7, 6, 5, 4, 3, 2, or 1 or 0.

In one embodiment, component (c) is present and (b) is absent. In another embodiment, component (b) is present and (c) is absent.

In one embodiment, (a), (b) and (c) are all present.

In one embodiment, (a) consists of 3, 2 or 1 monomers; (b) consists of 3, 2 or 1 monomers; and (c) consists of 3, 2 or 1 monomers.

In one embodiment, (a) consists of 1 monomer; (b) consists of 1 monomer; and (c) consists of 1 monomer.

In various embodiments, the molecular weight of each polar non-ionic macromer component of (a) is between about 400 and about 5000, about 500 and about 5000, about 1000 and about 5000, about 1000 and about 4000, about 1000 and 4500 or about 1500 and about 4500. In various embodiments, the molecular weight of each anionic component (b) is between about 50 and about 1000 and the molecular weight of each hydrophobic component (c) is between about 50 and about 1000.

In various embodiments, the molar ratio of (a) to (b)+(c) combined is at least about 1:21, at least about 1:30, a least about 1:40, at least about 1:50, at least about 1:60, at least about 1:70, at least about 1:80, or at least about 1:100. In one embodiment, the molar ratio of (a) to (b)+(c) combined is between about 1:>20 and about 1:100. In various embodiments, the molar ratio of (b) to (c) is less than about 10:1, less than about 1:1; less than about 1:10; less than about 1:20; less than about 1:50; or less than about 1:100; or the molar ratio of (b) to (c) is between about 10:1 and about 1:100.

In one embodiment, the polymer material interacts with human IgG in a manner that yields an IgG Fab exposure as determined by ELISA as set out in Example 2 of less than about 0.9, less than about 0.85, less than about 0.8, less than about 0.75, less than about 0.7, less than about 0.65, less than about 0.6, less than about 0.55, less than about 0.5, less than about 0.45, less than about 0.4, less than about 0.35, less than about 0.3, less than about 0.25, less than about 0.2 or less than about 0.15 of the value generated by D-PHI 1:1:7 (where D-PHI 1:1:7 is defined in example 1.)

Materials according to the present invention may be biodegradable and/or bioresorbable or substantially non-biodegradable.

In one aspect, there is provided a biocompatible composition comprising the reaction product of: between about 1 and about 60 percent by weight based on the total weight of the composition of at least one polar non-ionic macromer component; at least 40 percent by weight based on the total weight of the composition of anionic and hydrophobic component monomers; and wherein the anionic monomer component comprise between about 1 and about 90 percent by weight based on the combined hydrophobic and anionic components. In another aspect, there is provided a synthetic biocompatible polymer material comprising the reaction product of: (a) at least one polar non-ionic macromer component; (b) at least one anionic component; and (c) at least one hydrophobic component; wherein the polymer material interacts with human IgG in a manner that yields an IgG Fab exposure as determined by ELISA as set out in Example 2 of less than about 0.9, less than about 0.85, less than about 0.8, less than about 0.75, less than about 0.7, less than about 0.65, less than about 0.6, less than about 0.55, less than about 0.5, less than about 0.45, less than about 0.4, less than about 0.35, less than about 0.3, less than about 0.25, less than about 0.2 or less than about 0.15 of the value generated by D-PHI 1:1:7 (where D-PHI 1:1:7 is defined in example 1.)

In one embodiment, the macromer is the reaction product of at least one isocyanate compound, at least one polyol terminated with hydroxyl or amine groups and at least one vinyl coupling agent.

In various embodiments, the isocyanate compound may be Diisocyanatomethane; 1,4-Diisocyanatobutane; 1,1-Diisocyanatohexane; Hexamethylene diisocyanate (1,6-Diisocyanatohexane); Octamethylene diisocyanate (1,8-Diisocyanatooctane); 1,1-Diisocyanatoethane; 1,1-Diisocyanatobutane; 2,2-Dimethylpentane-1,5-diyl diisocyanate; 1,6-Diisocyanato-2,2,4-trimethylhexane; Trimethyl hexamethylene diisocyanate; Lysine diisocyanate; 1,1-Diisocyanatocyclohexane; Isophorone diisocyanate (5-Isocyanato-1-(isocyantomethyl)-1,3,3-trimethylcyclohexane); 4,4'-Methylenebis(cyclohexyl isocyanate); L-Lysine ethyl ester diisocyanate; 1,3-Phenylene diisocyanate; 1,4-Phenylene diisocyanate; 2-(diisocyanatomethyl) furan; Toluene 2,4-diisocyanate (2,4-Diisocyanatotoluene, 4-Methyl-m-phenylene diisocyanate, Tolylene 2,4-diisocyanate); Tolylene 2,5-Diisocyanate; Tolylene 2,6-Diisocyanate; m-Xylylene diisocyanate (1,3-Bis(isocyanatomethyl) benzene); 2,2-Diisocyanato-2,3-dihydro-1H-indene; 2,4,6-Trimethyl-1,3-phenylene diisocyanate; 1,5-Naphthalene diisocyanate; α,α,α',α'-Tetramethyl-1,3-xylylene diisocyanate (1,3,-Bis(1-isocyanato-1-methylethyl)benzene); 4,4'-Methylenebis(phenyl isocyanate) (4,4'-MDI, Bis(4-isocyanatophenyl)methane); 4,4'-Oxybis(phenyl isocyanate); 3,3'-Dimethyl-4,4'-Biphenylene Diisocyanate; 3,3'-Dimethyldiphenylmethane-4,4'-diisocyanate; 2,4,6-Triisopropyl-m-phenylene diisocyanate; 3,3'-Dimethoxy-4, 4'-biphenylene diisocyanate; 3,3'-(Tetrafluoroethane-1,2-diyl)bisphenyl diisocyanate; 1,1,1,2,2,3,3,4,4-nonafluoro-7, 7-diisocyanato-heptane; Tetraisocyanatosilane, Bis(1,1-dimethylethoxy)diisocyanato-silane; 1,1,3,3-tetraisocyanato-1,3-dimethyl disiloxane; 2-Propenoic acid, 2-methyl-, 3-(triisocyanatosilyl)propyl ester; 2-Propenoic acid, 2-methyl-, 4-[3-(triisocyanatosilyl)propyl]phenyl ester; 1,2,2-Triisocyanatobutane, Hexamethylene diisocyanate-biuret; Hexamethylene diisocyanate isocyanurate; 2,2'-Methylenebis[6-(o-isocyanatobenzyl)phenyl]diisocyanate; 2,4,6-trioxotriazine-1,3,5(2H,4H,6H)-triyl)tris(methyl-m-phenylene) isocyanate; Poly[methylene(polyphenyl) isocyanate]; Poly(hexamethylene diisocyanate); Polycarbonate-based diol MDI terminated Prepolymer; Polyether based diol HDI terminated Prepolymer; Poly(propylene glycol), tolylene 2,4-diisocyanate terminated (isocyanate~3.6 wt. %); Polycarbonate-based diol PPDI terminated Prepolymer; or Poly(1,4-butanediol)tolylene 2,4-diisocyanate terminated (1.9 wt. % isocyanate).

In various embodiments, the at least one polyol terminated with hydroxyl or amine groups comprises polyethylene oxide; polypropylene oxide; polytetramethylene oxide; polyisobutylene; polybutadiene; polyethylene adipate; polytetramethylene adipate; polycaprolactone; polydimethylsiloxane; polycarbonate; polysiloxane; polyethylenebutylene; polyester; polyether sulfone; polyurethane; polyurea; polyamide; polyalkylene oxide; polyvinyl derivatives; polypeptide derivatives; polysaccharide derivatives; polyethylenebutylene; 4-butanediol; ethylene diamine; 4,4' methylene, bis(2-chloroaniline); ethylene glycol; hexanediol; butane diol; ethylene diamine; hexamethylene diamine; hexamethylene dicarboxylic acid; lysinate; hexane diol; 2,5 diaminobenzenesulfonic acid; 4,4'diamino 2,2'-biphenyl disulfonic acid; 1,3-diamino 2-hydroxypropane; N-(2-aminoethyl)-3-aminopropane sulfonate; dihydroxy vinyl derivatives; dihydroxy diphenylsulfone; hexamethylene diol; 1,5 pentanediol; 2,2-dimethyl-1,3 propanediol; 1,2-diamino-2 methylpropane; 3,3,-diamino-N-methyldipropylamine; 1,4 diaminobutane; 1,7 diaminoheptane; 1,8 diaminooctane; glutaryl dichloride; or adipoyl dichloride In various embodiments, the at least one vinyl coupling agent may be a vinyl alcohol, an alkyl amine with vinyl groups, a vinyl amine, hydroxypropyl (meth)acrylate, 2,3-dihydroxypropyl (meth)acrylate, 1,4-butanediol monoacrylate, (poly)ethylene glycol mono(meth)acrylate, 3-aminopropyl vinyl ether, or 2-hydroxyethyl methacrylate (HEMA).

In one embodiment, the macromer is the reaction product of poly(hexamethylene carbonate) diol, lysine diisocyanate and 2-hydroxyethyl methacrylate.

In various embodiments, the anionic component is a vinyl monomer with mono acid function such as methacrylic acid, vinyl phosphoric acid, styrene sulphonic acid or the like; vinyl monomers with di-acids such as itaconic acid, maleic acid or the like; or vinyl monomers with tri-acids such as tricarballylic acid, tricarboxylic acid or the like. The anionic component may also be a methacrylic acid derivative; 2-(methacryloyloxy)ethyl phosphate; 2(methacryloyloxy) ethyl succinate, [3-(methacryloylamino)propyl]trimethyl ammonium chloride; or 2-(methacryloyloxy)ethyl]trimethylammonium methyl chloride. The methacrylic acid derivative may be an amino-acid derivative. The anionic component may be methacrylic acid.

In one embodiment, the hydrophobic component is an alkyl methacrylate, wherein the alkyl chain is linear or branched, saturated or unsaturated, and wherein the number of carbons is less than 12. In one embodiment, the alkyl chain is non-aromatic. In various embodiments, the hydrophobic component may be methyl, propyl, butyl, iso-butyl or t-butyl methacrylate. The hydrophobic component may be methyl methacrylate. In one embodiment, the hydrophobic component comprises a pendant non-aromatic group.

In one embodiment, the polymer material is synthesized using a free radical initiator. The free radical initiator may be selected from diacyl peroxides, peroxy esters, dialkyl peroxides, dialkyl peroxydicarbonates, tert-alkylhydroperoxides, and ketone peroxides. In various embodiments, the free radical initiator is dibenzoyl peroxide, diisobutyrul peroxide, t-butyl peracetate, dicumyl peroxide, di-sec-butyperoxydicarbonate, methyl ethyl ketone peroxide, benzyl peroxide or 1,1'-azobis(cyclohexanecarbonitrile).

In one embodiment, a light curing system is used to polymerize the resin. Photopolymerization may be initiated with camphorquinone and 2-(dimethylamino)ethyl methacrylate.

In one embodiment, the biocompatible polymer material further includes one or more additives in admixture, suitably selected from antioxidants, fillers, cross-linkers, plasticizers, nucleating agents, or pigments.

In one embodiment, the biocompatible polymer material is in admixture with a therapeutic agent.

The additive(s) or therapeutic agent may be present in an amount of less than 50, less than 40, less than 30, less than 20, less than 10, less than 5 or less than 1 percent by weight of the polymeric material.

In certain embodiments, materials according to the present invention may be in the form of a formed object, a coating, a film, a foam, a gel, or a particulate.

Also provided herein are medical devices comprising the polymer materials disclosed herein, including implants, tissue engineering scaffolds, biosensors and therapeutic delivery devices.

Also provided herein is a method of decreasing IgG Fab exposure in a synthetic biocompatible polymer material exposed to IgG, the polymer material comprising the reaction product of:
  (a) at least one polar non-ionic macromer component; and one or both of
  (b) at least one anionic component; and (c) at least one hydrophobic component;

the method comprising increasing the ratio of (b) plus (c) combined to (a) such that the polymer material interacts with human IgG in a manner that yields a lower IgG Fab exposure as determined by ELISA as compared to the reaction product of (a), (b) and (c) with a lower ratio of (b) plus (c) combined to (a). In one embodiment, (b) is present and (c) is absent. In one embodiment, (c) is present and (b) is absent. In one embodiment of the method, both (b) and (c) are present. The method is suitably applied to a polymer material as described herein, wherein the at least one non-ionic macromer component, at least one anionic compound and at least one hydrophobic component are as described herein.

BRIEF DESCRIPTION OF THE DRAWINGS

FIG. 1 shows the synthesis of a polymeric material according to one embodiment.

FIG. 2 shows IgG Fab quantification. Standard tissue culture polystyrene (TCPS) film used as control and 1:5:15 D-PHI film used as baseline (white bars) for different D-PHI film formulations (grey bars). Bars represent mean±s.e. n=9 for each film. *p<0.0005; **p<0.05 for all D-PHI samples vs. TCPS.

FIG. 3 shows total IgG adsorbed per surface area. Representative D-PHI formulations (grey bars) compared to D-PHI-1:5:15 formulation (white bar). Bars represent mean±s.e. n=9 for each film.

FIG. 4 shows the elongation percentage at break in D-PHI-1:5:15 (white bar) and D-PHI 1:1:7 (grey bar) films. Bars represent mean±s.e. n=10 for each film. *p<0.0005.

FIG. 5 shows the quantification of monocyte attachment to IgG-coated D-PHI-1:5:15 films, D-PHI 1:1:7 films, and TCPS surfaces normalized to each respective non-coated surface. Bars represent mean±s.e. n=18 (3 donors). *p<0.05. p<0.05 and *p<0.0001 in IgG-coated vs. non-coated controls.

FIG. 6 shows SEM images of monocytes on non-coated and preadsorbed IgG surfaces of D-PHI 1:5:15 and D-PHI 1:1:7. Arrows indicate examples of pseudopodia of activated monocytes.

FIG. 7 shows quantification of monocyte spreading on non-coated and preadsorbed IgG surfaces of D-PHI 1:5:15 and D-PHI 1:1:7. Bars represent mean±s.e. n=9 images, 3 donors.

FIG. 8 shows quantification of pseudopodic area as a percentage of total cell area on non-coated and preadsorbed IgG surfaces of D-PHI 1:5:15 and D-PHI 1:1:7. Bars represent mean±s.e. n=9 images, 3 donors. *p<0.05 and **p<0.00001 between formulations. †<0.01 and ††<0.00001 with control surfaces within formulations.

FIG. 9 shows monocyte inflammatory-like response to adsorbed proteins at day 1 on (a) TCPS and (b) D-PHI, day 3 on (c) TCPS and (d) D-PHI. All media conditions (no serum, AHS, FBS) aggregated, to emphasize the ratio dependence of type of coating. Bars represent mean±s.e. n=24 across 3 donors (8 samples, 3 conditions each).

FIG. 10 shows total IgG per area (a) and IgG Fab (b) quantification. (a): all values normalized to surface area and then PLGA. (b) Adsorbed IgG treated with 10% AHS (black bars), 10% FBS (grey bars), and no serum (white bars). Bars represent mean±s.e. n=24 across 3 donors for AHS, and n=8 for FBS and No Serum samples.

FIG. 11 shows IgG Fab normalized to Total IgG on TCPS and D-PHI without serum incubation. Bars represent mean±s.e. n=8.

FIG. 12 are SEM images showing monocytes on TCPS have a different morphology at day 3 depending on condition. Each column represents a specific protein adsorption coating (IgG vs. fibronectin vs. no coating), and each row represents serum content of media (no serum vs. 10% AHS vs. 10% FBS). All photos taken 10 kV. Scale bars represent 30 μm.

FIG. 13 are SEM images showing monocytes on D-PHI have similar morphology across different protein and material conditions. Each column represents a specific protein adsorption coating (IgG vs. fibronectin vs. no coating), each row represents serum content of media (no serum vs. 10% AHS vs. 10% FBS). All photos taken 10 kV. Scale bars represent 30 µm.

Figure 14:
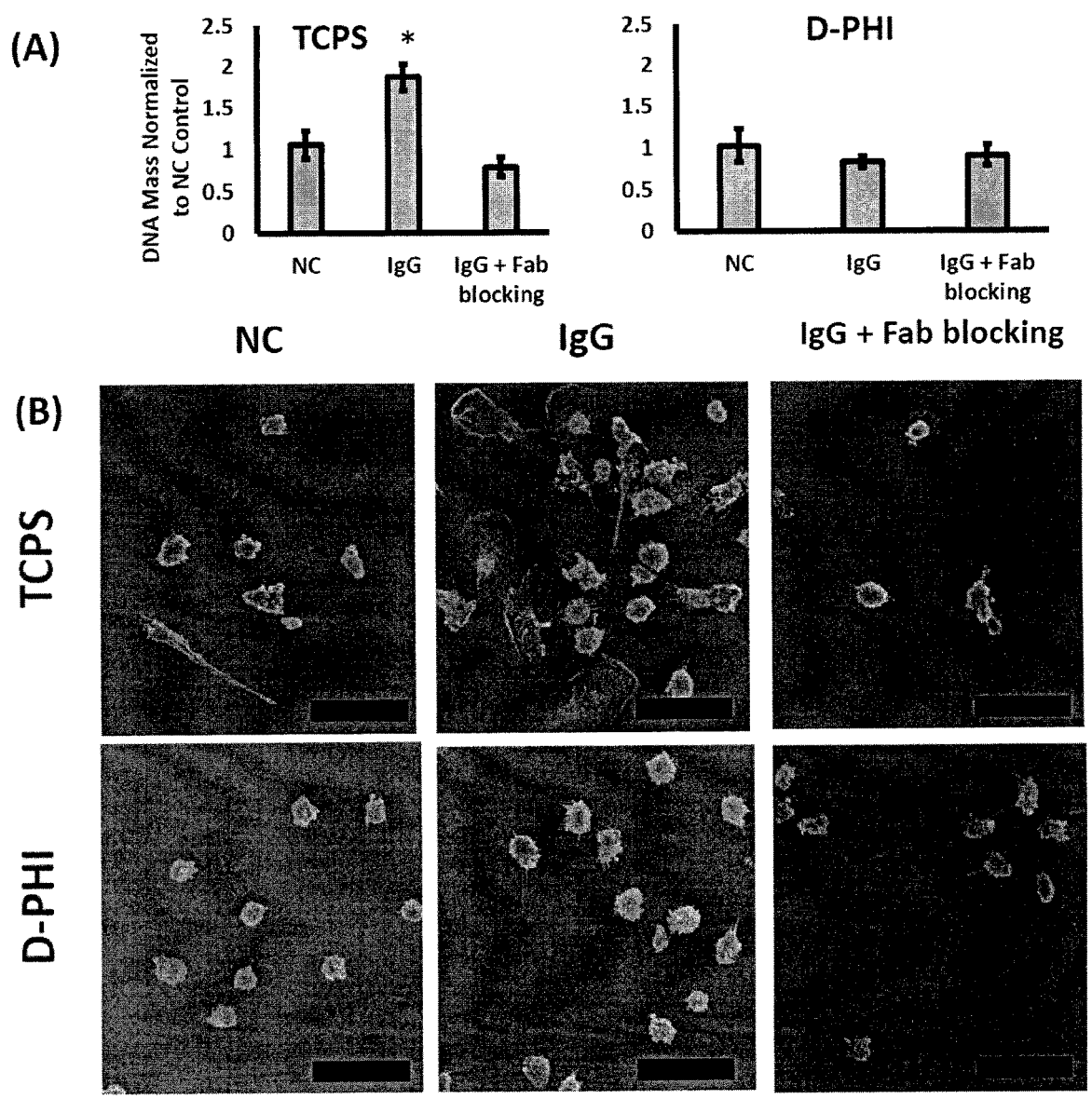

FIG. 14 shows DNA mass quantification (A) and SEM images (B) for monocytes seeded on IgG pre-adsorbed and non-coated D-PHI and TCPS surfaces, and exposed or not exposed to a Fab-specific blocking antibody. N=9, from 3 donors. Data represent the mean±S.E. Scale bars represent 30 µm.

Figure 15:
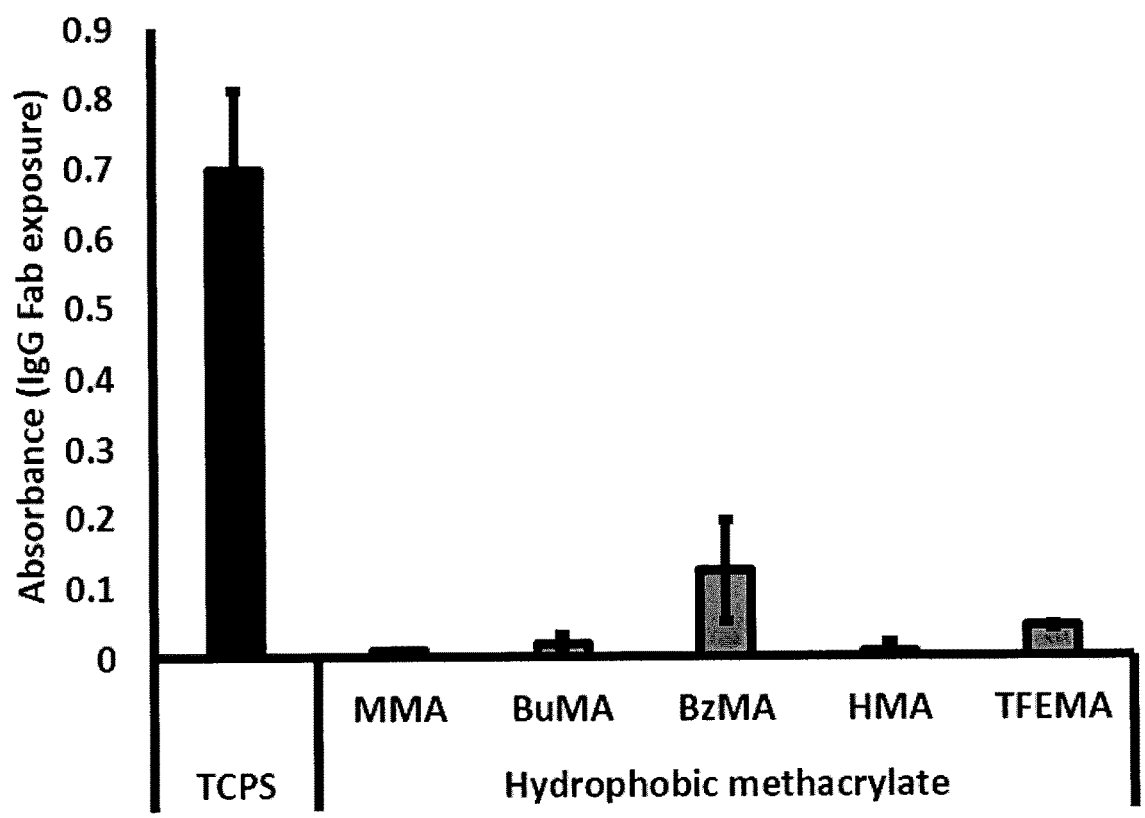

FIG. 15 shows IgG Fab quantification for different D-PHI formulations compared to the 1:5:15 (divinyl oligomer (DVO):methacrylic acid (MAA):methyl methacrylate (MMA)) formulation and a TCPS control. For all D-PHI formulations, the 1:5:15 molar ratio has been maintained, but the hydrophobic methacrylate has been varied to be either methyl methacrylate (MMA), butyl methacrylate (BuMA), benzyl methacrylate (BzMA), hexyl methacrylate (HMA) or trifluoroethyl methacrylate (TFEMA). Data are the mean±s.d. n=3.

Figure 16:
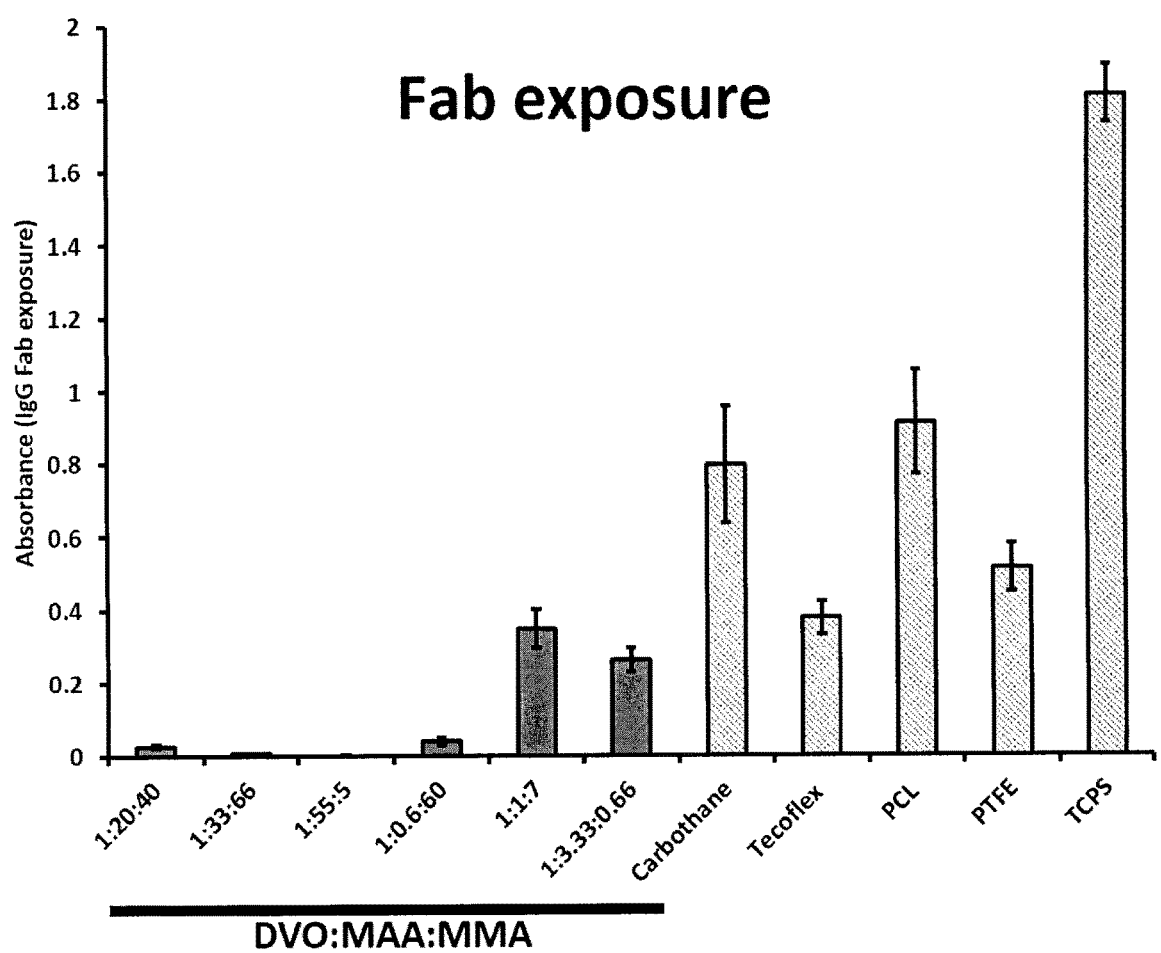

FIG. 16 shows IgG Fab quantification for different D-PHI formulations compared to commercial biomaterials as controls, including TCPS, polycaprolactone (PCL), polytetrafluoroethylene (PTFE), and the commercial polyurethanes Carbothane® and Tecoflex®. Bars represent the mean±s.e. n=9 for all samples except PTFE (n=6).

Figure 17:
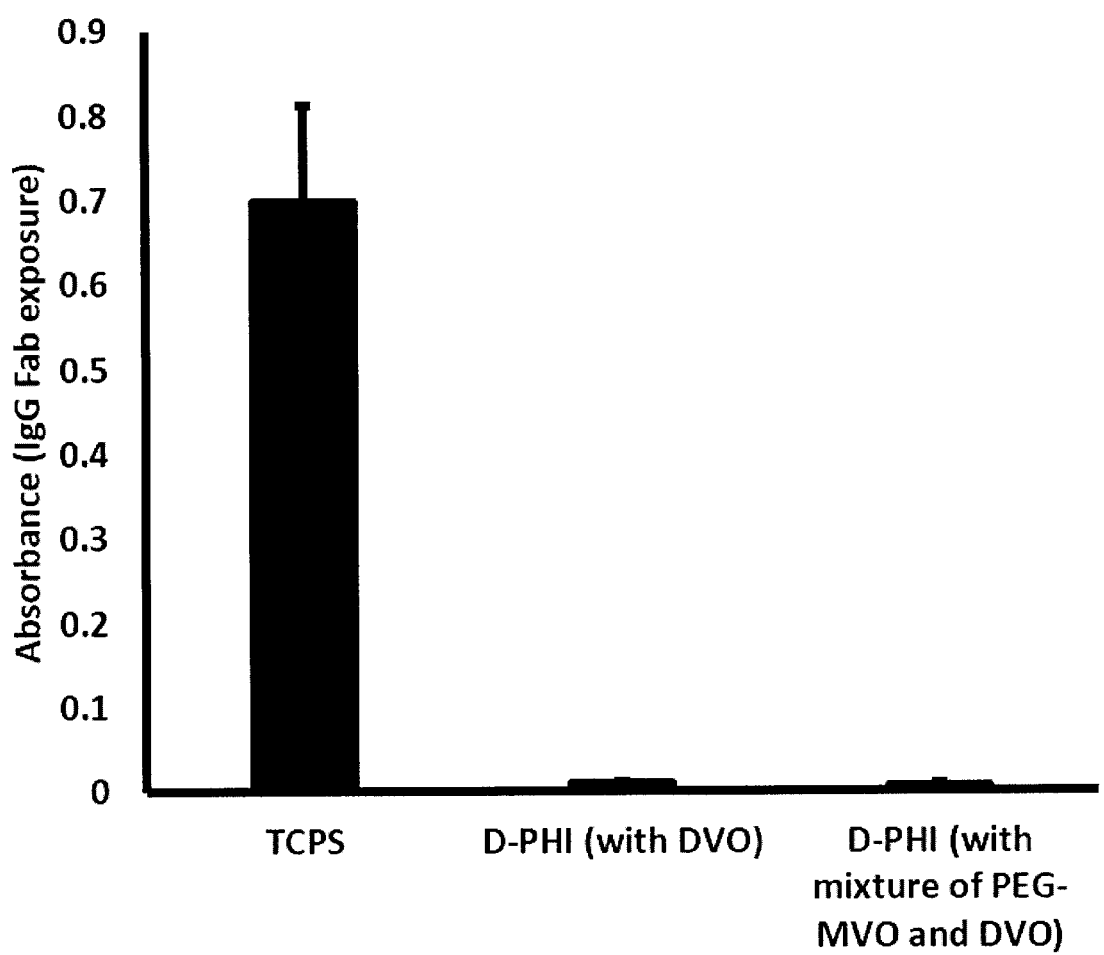
Figure 18:
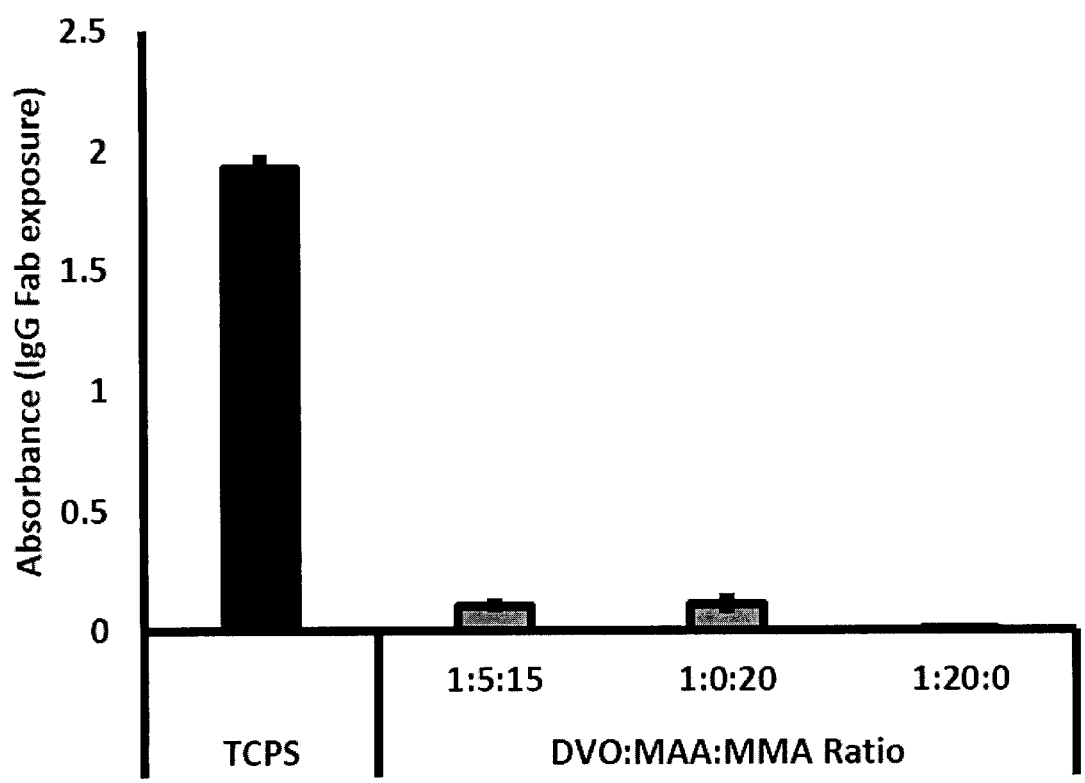

FIG. 17 shows IgG Fab quantification for different D-PHI formulations using the 1:5:15 (a):(b):(c) molar ratio where (b) is MAA, (c) is MMA, and (a) is either DVO or a mixture of DVO and Polyethylene glycol-Monovinyl Oligomer (PEG-MVO). Data are the mean±s.d. n=3. FIG. 18 shows IgG Fab quantification for different D-PHI formulation where either component (b) or component (c) has been removed from the monomer mixture, such that the formulation consists of only (a)+(b) or (a)+(c). Data are the mean±s.d. n=3.

FIG. 18 shows IgG Fab quantification for different D-PHI formulations where either component (b) or component (c) has been removed from the monomer mixture, such that the formulation consists of only (a)+(b) or (a)+(c). Data are the mean±s.d. n=3.

DETAILED DESCRIPTION

Immunoglobulins and in particular Immunoglobulin G are important blood proteins influencing the processes of innate immune and inflammatory response. Specifically, Immunoglobulin G (IgG) antibody isotype is a 150 kDa glycoprotein that consists of two heavy chains (50 kDa) and two light chains (25 kDa) connected by disulfide bonds across the so-called hinge regions. The resulting Y-shaped IgG antibody is characterized by its particular enzymatic fragments: the constant Fc region (recognized by immune cells bearing Fcγ receptors) and variable Fab regions (antigen-binding sites). The IgG class of immunoglobulins is the most widespread in the extracellular fluids, accounting for 75% of the total immunoglobulins in the serum of healthy individuals. IgG is activated following repeated contact with antigens and is a significant effector molecule of the adaptive immune response. The major effector functions of IgG involve the activation of the complement system and opsonisation to induce phagocytosis of marked pathogens; the Fab and Fc regions assist in the recognition of antigens and in the recruitment and binding of specific immune cells. Its activation has secondary effects that influence many cell types involved in healing and blood responses. IgG Fc receptors can be found on many cell types, including monocytes, macrophages, neutrophils, eosinophils, dendritic cells, B cells, mast cells, hepatocytes, epithelial cells, endothelial cells, platelets, and fibrocytes. Interactions of IgG with the Fc receptors are associated with functions such as phagocytosis, cell activation, inhibition of cellular activity, and adhesion. Other effects of IgG have been shown to be mediated by IgG immune complexes involving either the whole IgG molecule or the F(ab')$_2$ fragment (antibody-antigen binding), a well as by the Fab region of the IgG molecule, which is of particular importance for regulating the adhesion of macrophages to biomaterial surfaces.

Monocytes/macrophages are cell populations of particular interest because they are considered key mediators of inflammation and the FBR. The early stages of inflammation are characterized by the recruitment of leukocytes from the systemic circulation. As the inflammatory response progresses, monocytes extravasate and migrate to a biomaterial implantation site, guided by chemoattractants and chemokines secreted by the cells already present at the site, such as vascular smooth muscle cells, endothelial cells, neutrophils, and other immune cells. Monocytes are able to adhere to the biomaterial surface by interactions with the adsorbed protein layer. Adherent monocytes release characteristic protein profiles; specific cytokines, such as tumor necrosis factor alpha (TNF-α) and interleukin-10 (IL-10) are essential during the inflammatory response and can be used as markers of monocyte activation. In addition, since monocytes differentiate into macrophages, monocytes are precursors to one of the key immune cells involved in the FBR.

Macrophages are considered the primary mediators of implant-associated inflammation and the FBR. Depending on their location, macrophages possess different morphological and functional characteristics. They are functionally and phenotypically diverse and may respond uniquely depending on the environment and signaling molecules present. They can be classified as classically activated, wound-healing, or regulatory. When activated, macrophages secrete a wide array of agents such as proteolytic enzymes, reactive oxygen species, and cytokines. These substances can activate cell populations including other macrophages, neutrophils, and fibroblasts as well as contribute to the degradation of the biomedical device. However, the ability of macrophages to modify their activation state imparts them with the ability to influence wound-healing and the host response. Long-term functionality of the biomedical device requires regulation of macrophage activity.

As the number of adherent macrophages continues to increase at the tissue-biomaterial interface, the macrophages fuse to form multinucleated foreign body giant cells (FBGCs). The presence of FBGCs represents a stage known as frustrated phagocytosis in which foreign objects or particulate from the biomaterial cannot be phagocytosed by the macrophages. Instead, they conglomerate to become FBGCs, which allows them to remain adherent to the biomaterial and prevents apoptosis or anoikis. Formation of FBGCs requires a biomaterial surface conducive for fusion; the surface must be adsorbed with the appropriate proteins to enable the necessary phenotypic transformation of adherent macrophages to become FBGCs. FBGCs contribute to the inflammatory response by secreting cytokines, reactive oxygen species, and degradative enzymes, which also contribute to the degradation and possible failure of the biodevice.

Previously, the objective of implantable materials was 'inertness' and avoiding unnecessary interaction with the tissue. However, current knowledge regarding the immune system in response to biomedical device implantation suggests that the concept of 'inertness' does not exist. Rather, the biomaterial should be designed such that tissue-material interactions are appropriately controlled to elicit a desirable immune response. A controlled immune response would enhance the biomaterial's acceptance by the host and eventual biointegration.

There remains a need for materials that are biocompatible and interact with proteins and in particular immune related proteins such as the immunoglobulin proteins, in a manner that leads to having a more predictable reaction to the body's cells, tissues, and body fluids, and specifically agents related to the immune (specific or non-specific) response, a more desirable immune response and/or a more controllable immune response than commonly used biomaterials.

In one aspect, the term "biocompatible" means either a non-degradable, or bioresorbable or biodegradable material that will have less adverse effect(s) on cells, tissue or function in vivo as compared to a known biomaterial. In one embodiment, this known biomaterial is standard tissue culture polystyrene (TCPS), polycaprolactone (PCL), polytetrafluoroethylene (PTFE), or poly(lactic-co-glycolic acid) (PLGA). In one embodiment, this adverse effect is characterized by less IgG Fab exposure as compared to a known biomaterial when the material interacts with human IgG, which may be determined by a method provided herein. In one embodiment, "biocompatible" means either a non-degradable, or bioresorbable or biodegradable material that will have less adverse effect(s) on cells, tissue or function in vivo as compared to the commercial polyurethane Carbothane® or Tecoflex®. In one embodiment, this adverse effect is characterized by less IgG Fab exposure when the material interacts with human IgG, which may be determined by a method provided herein. In one embodiment, "biocompatible" means either a non-degradable, or bioresorbable or biodegradable material that will have less adverse effect(s) on cells, tissue or function in vivo as compared to D-PHI 1:1:7 (where D-PHI 1:1:7 is defined in example 1). In one embodiment, this adverse effect is characterized by less IgG Fab exposure when the material interacts with human IgG, which may be determined by a method provided herein.

As used herein, the term "curable" means that a material can be changed from its initial state and set to a final form to achieve strong inter-atomic bonding through energy input (i.e. thermal, radiation, chemical, air or light, but not limited to these).

As used herein, the term "polar non-ionic macromer" is a molecule of greater than about 400 molecular weight but less than about 5000, with a segment of the molecule that contains repeat monomer units, and at least two polar functional groups, and at least two reactive groups which can be readily covalently coupled with similar type groups (e.g. vinyl groups) to yield a material. In one embodiment, the polar non-ionic macromer is generated with molecules containing isocyanate groups. The molecules do not contain free ionic function but may be precursors to said ionic function upon hydrolysis of protecting groups within the precursors. Said protecting groups may be used to couple covalently or non-covalently drugs, biological agents (peptides, or other pendent molecules; or contribute to the ionic content of cured polymers.)

As used herein, the term "non-biodegradable" implies a biomaterial that undergoes less than 1% degradation within the first month of implantation in a subcutaneous rate implant model such as that reported on by McBane J E, Sharifpoor S, Kuihua C, Labow R S, and Santerre J P, Evaluating the biodegradation and in vivo biocompatibility of a degradable polar/hydrophobic/ionic polyurethane for use in vascular tissue engineering, *Biomaterials*. 32, 6034-44 (2011).

IgG is known to be important for host-biomaterial interactions. IgG that has adsorbed to biomaterial surfaces can support macrophage [Jenney C R and Anderson J M. Adsorbed IgG: a potent adhesive substrate for human macrophages. *J Biomed Mater Res* 2000; 50(3):281-90] and neutrophil adhesion [Wettero J, Bengtsson T, Tengvall P. Complement activation on immunoglobulin G-coated hydrophobic surfaces enhanced the release of oxygen radicals from neutrophils through an actin-dependent mechanism. *J Biomed Mater Res* 2000; 51:742-741; Bastian F, Stelzmueller M, Kratochwill K, Kasimir M, Simon P, Weigel G. IgG deposition and activation of the classical complement pathway involvement in the activation of human granulocytes by decellularized porcine heart valve tissue. *Biomaterials* 2008; 29:1824-1832], as well as lead to enhanced FBGC formation, leading to a cellular phenotype associated with an unresolved, chronic inflammatory response [Shen M, Garcia I, Maier R, Horbett T. Effects of adsorbed proteins and surface chemistry on foreign body giant cell formation, tumor necrosis factor alpha release and procoagulant activity of monocytes. *J Biomed Mater Res A* 2004; 70A:533-541]. In addition to mediating adhesion, adsorbed IgG also supports the activation of macrophages and neutrophils through the release of pro-inflammatory cytokines and reactive oxygen species [Wettero et al., 2000; Shen et al., 2004; Tang L, Lucas A, Eaton J. Inflammatory responses to implanted polymeric biomaterials—role of surface-adsorbed immunoglobulin g. *J Lab Clin Med* 1993; 122:292-300], as well as supporting maturation of dendritic cells [Carillo-Conde B R, Ramer-Tait A E, Wannemuehler M J, Narasimhan B. Chemistry-dependent adsorption of serum proteins onto polyanhydride microparticles differentially influences dendritic cell uptake and activation. *Acta Biomater* 2012; 8:3618-3628]. Nanoparticles that have deposited IgG are also more susceptible to macrophage phagocytosis [Yang A, Liu W, Li Z, Jiang L, Xu H, Yang X. Influence of polyethyleneglycol modification on phagocytic uptake of polymeric nanoparticles mediated by immunoglobulin g and complement activation. *Journal of Nanoscience and Nanotechnology* 2010; 10:622-628]. IgG also has the ability to support the function of non-immune cells, such as supporting adhesion of endothelial cells [Bouafsoun A, Helali S, Othmane A, Kerkeni A, Prigent A, Jaffrezic-Renault N, et al. Evaluation of endothelial cell adhesion onto different protein/gold electrodes by EIS. *Macromolecular Bioscience* 2007; 7:599-610], as well as platelet adhesion and fragmentation [De Paoli S H, Diduch L L, Tegegn T Z Orecna M, Strader M B, Kamaukhova E, Bonevich J E, Holada K, Simak J. The effect of protein corona composition on the interaction of carbon nanotubes with human blood platelets. *Biomaterials* 2014; 35(24):6182-6194; DiFazio L, Stratoulias C, Greco R, Haimovich B. Multiple platelet surface-receptors mediate platelet adhesion to surfaces coated with plasma proteins. *J Surg Res* 1994; 57:133-137], suggesting an important role in the coagulation process. In addition to supporting specific cellular activity and phenotypes, adsorbed IgG is also an important regulator of complement activation [Wettero et al., 2000; Bastian et al., 2008].

The present inventors have determined that polar hydrophobic ionic materials and, in particular, polar hydrophobic ionic polyurethanes having a minimum ratio of hydrophobic and anionic components to the remainder of the polymer components exhibit reduced IgG Fab exposure.

The present inventors have further demonstrated that monocyte attachment to and/or activation of monocytes attached to a polar hydrophobic ionic polymeric material and, in a particular embodiment, a polar hydrophobic ionic polyurethane (PHI), can be reduced by providing a minimum ratio of hydrophobic and anionic components to the remainder of the polymer component(s). In one embodiment, the polar hydrophobic ionic polyurethane is non-degradable (nD-PHI), and in another it is degradable (D-PHI).

As detailed in the Examples, PHI films exhibiting one or both of high hydrophobicity or high ionic properties relative to the macromer, exhibit a reduced Fab exposure when compared to PHI films having low hydrophobicity and low ionic properties. The inventors have further demonstrated that Fab exposure in PHI is correlated with cell adhesion and specifically monocyte adhesion and activation, the latter in turn being associated with chronic inflammatory responses. Accordingly, in one embodiment, the present invention is directed to a polymeric biomaterial that exhibits a reduced inflammatory cell response as compared to one or more known biomaterials e.g. poly(lactic-co-glycolic acid) (PLGA), a commonly used biodegradable biomaterial, and standard tissue culture polystyrene (TCPS), a non-biodegradable biomaterial.

In one aspect, there is provided a synthetic biocompatible polymer material comprising, consisting essentially of, or consisting of, the reaction product of:
(a) at least one polar non-ionic macromer component; and one or both of:
(b) at least one anionic component; and
(c) at least one hydrophobic component;
the molar ratio of (a) to (b) and (c) combined being at least about 1:10; the molar ratio of (b) to (c) being between about 20:1 and 1:100; and the maximum combined number of components (a), (b) and (c) in the polymer being 9. In one embodiment, the molar ratio of (a) to (b) and (c) combined is at least 1:>20.

In some cases, the character of (b) or (c) may be contained within (a) and in such cases one of (b) or (c) may be optional. More specifically, in some embodiments, (b) may be omitted where (a), while comprising a macromer that is non-ionic includes an anionic pendant group such that a portion of the molecule comprises an anionic functionality. For example, the macromer of (a) can be considered to contain the functionality normally found in (b) where the macromer (a) contains lysine diisocyate and the methyl ester of lysine diisocyanate has been hydrolyzed to yield a pendant anionic carboxylic acid group. In other embodiments, (c) may be omitted where (a), while comprising a polar macromer includes a hydrophobic portion such that a portion of the molecule comprises hydrophobic functionality. For example, the macromer of (a) can be considered to contain the hydrophobic functionality normally contained in (c) where the macromer (a) contains a soft segment of poly(tetramethylene oxide), wherein component (a) will have hydrophobic character in addition to the polar character provided by the urethane bonds.

The maximum number of monomers comprising (a), (b), or (c) is 9. Accordingly, the number of monomers comprising (a) may be 8 (where (b) or (c) is absent), 7, 6, 5, 4, 3, 2, or 1. The number of monomers comprising (b) may be 8 (where (c) is absent), 7, 6, 4, 3, 2, 1 or 0. The number of monomers comprising (c) may be 8 (where (b) is absent), 7, 6, 5, 4, 3, 2, or 1 or 0.

In one embodiment, the biocompatible polymer material is biodegradable and/or bioresorbable. In another embodiment, the biocompatible polymer material is substantially non-biodegradable.

In other embodiments, a maximum of three different non-ionic macromer components, a maximum of three different anionic components, and a maximum of three different hydrophobic components are used. In one aspect, these maximums are pragmatic, based on control of the reaction process and resulting product.

In other embodiments, the molar ratio of component (a) to the sum of components (b) and (c) combined is at least about 1:21, at least about 1:25, at least about 1:30, at least about 1:35, at least about 1:40, at least about 1:45, at least about 1:50, at least about 1:55, at least about 1:60, at least about 1:65, at least about 1:70, at least about 1:75, at least about 1:80, at least about 1:85, at least about 1:90, at least about 1:100.

In other embodiments, the molar ratio of component (b) to component (c) is between about 20:1 and about 1:100, 1:90, about 1:80, about 1:70, about 1:60, about 1:50, about 1:40, about 1:30, about 1:20, about 1:10, about 1:1, or about 10:1.

In other embodiments, the ratio of component (b) to component (c) is between about 1:1 and about 1:10, between about 1:1 and about 1:5, between about 1:1 and about 1:2.

In various embodiments, the macromer has a molecular weight of between about 400 and about 5000, about 500 and about 5000, about 1000 and about 5000, about 1000 and about 4000, about 1000 and 4500 or about 1500 and about 4500.

In another aspect, there is provided a biocompatible composition comprising, consisting essentially of, or consisting of, the reaction product of: between about 1 and about 60 percent by weight based on the total weight of the composition of at least one polar non-ionic macromer component; at least 40 percent by weight based on the total weight of the composition of anionic and hydrophobic component monomers; and whereby the anionic monomer component comprises between about 1 and about 90 percent by weight based on the combined hydrophobic and anionic components.

In other embodiments, the at least one polar non-ionic macromer component is present in an amount between about 1%, about 2%, about 5% or about 10% and about 20%, about 25%, about 30%, about 35%, about 40%, about 45%, about 50%, about 55% or about 60% by weight, based on the total weight of the composition.

In other embodiments, the anionic monomer component comprises between about 1, about 2, about 5 or about 10 and about 20, about 30, about 40, about 50, about 60, about 70, about 80 or about 90 percent by weight based on the combined hydrophobic and anionic components In one embodiment, the reaction product is a polyester such as a polylactide, polylactone, a polycondensate of glycol and a dicarbonic acid, or poly(butylenes terephthalate); a polyol; a polycarbonate; a polyanhydride; a poly(a-cyanoacrylate); a polyphosphazene; or a poly(orthoester).

In one embodiment, the reaction product is a polar non-ionic hydrophobic polyurethane. Polyurethanes are synthetic block copolymers characterized by the presence of a urethane linkage created in a condensation reaction (step-growth polymerization). Polyurethanes can be linear, branched, or cross-linked. Polyurethanes are copolymers and contain two repeating segments; a hard segment of the polyurethane (the isocyanate), which endows the biomaterial with mechanical strength and a soft segment (the polyol), which provides flexibility. The soft and hard segments can microphase separate to form soft and hard phases; these phases provide the polymer with both flexibility and strength. The combination of segments manifests itself in the bulk material composition and surface microstructure. The differences in polarity of the hard and soft segments affect the hydrophilic-hydrophobic balance of the biomaterial. Furthermore, the soft segments are mobile and will optimize their location to minimize the free energy at the surface of the material. The copolymer structure and the composition of its monomers provide a polyurethane with its unique in vivo properties and biocompatibility.

In one embodiment, the polar non-ionic macromer comprises a soft segment and a hard segment. In one embodiment, the hard segment is derived from an isocyanate and vinyl monomers.

In one embodiment, the isocyanate is not particularly restricted. In one embodiment, the isocyanate has a molecular between about 100 and about 1000. In one embodiment, the isocyanate component is one or more of a linear diisocyanate e.g. Diisocyanatomethane, 1,4-Diisocyanatobutane, 1,1-Diisocyanatohexane, Hexamethylene diisocyanate (1,6-Diisocyanatohexane), and Octamethylene diisocyanate (1,8-Diisocyanatooctane); a branched alkane diol, e.g. 1,1-Diisocyanatoethane, 1,1-Diisocyanatobutane, 2,2-Dimethylpentane-1,5-diyl diisocyanate, 1,6-Diisocyanato-2,2,4-trimethylhexane, Trimethyl hexamethylene diisocyanate, and Lysine diisocyanate; a cyclic diisocyanate, e.g. 1,1-Diisocyanatocyclohexane, Isophorone diisocyanate (5-Isocyanato-1-(isocyantomethyl)-1,3,3-trimethylcyclohexane), 4,4'-Methylenebis(cyclohexyl isocyanate—mixture of isomers, and L-Lysine ethyl ester diisocyanate; an aromatic diisocyanate e.g. 1,3-Phenylene diisocyanate, 1,4-Phenylene diisocyanate, 2-(diisocyanatomethyl)furan, Toluene 2,4-diisocyanate (2,4-Diisocyanatotoluene, 4-Methyl-m-phenylene diisocyanate, Tolylene 2,4-diisocyanate), Tolylene 2,5-Diisocyanate, Tolylene 2,6-Diisocyanate, m-Xylylene diisocyanate (1,3-Bis(isocyanatomethyl)benzene), 2,2-Diisocyanato-2,3-dihydro-1H-indene, 2,4,6-Trimethyl-1,3-phenylene diisocyanate, 1,5-Naphthalene diisocyanate, α,α,α',α'-Tetramethyl-1,3-xylylene diisocyanate (1,3,-Bis(1-isocyanato-1-methylethyl)benzene), 4,4'-Methylenebis(phenyl isocyanate) (4,4'-MDI, Bis(4-isocyanatophenyl)methane), 4,4'-Oxybis(phenyl isocyanate), 3,3'-Dimethyl-4,4'-Biphenylene Diisocyanate, 3,3'-Dimethyldiphenylmethane-4,4'-diisocyanate, 2,4,6-Triisopropyl-m-phenylene diisocyanate, and 3,3'-Dimethoxy-4,4'-biphenylene diisocyanate; a fluorine-containing diisocyanate, e.g. 3,3'-(Tetrafluoroethane-1,2-diyl)bisphenyl diisocyanate and 1,1,1,2,2,3,3,4,4-nonafluoro-7,7-diisocyanato-heptane; a silicone-containing poly-isocyanate, e.g. Tetraisocyanatosilane, Bis(1,1-dimethylethoxy)diisocyanato-silane, 1,1,3,3-tetraisocyanato-1,3-dimethyl disiloxane, 2-Propenoic acid, 2-methyl-, 3-(triisocyanatosilyl)propyl ester, and 2-Propenoic acid, 2-methyl-, 4-[3-(triisocyanatosilyl)propyl]phenyl ester; a tri or tetra isocyanate, e.g. 1,2,2-Triisocyanatobutane, Hexamethylene diisocyanate-biuret, Hexamethylene diisocyanate isocyanurate, 2,2'-Methylenebis[6-(o-isocyanatobenzyl)phenyl]diisocyanate, and 2,4,6-trioxotriazine-1,3,5(2H,4H,6H)-triyl)tris(methyl-m-phenylene) isocyanate; a polyisocyanate, e.g. Poly[methylene(polyphenyl) isocyanate] and Poly(hexamethylene diisocyanate); or a diisocyanate-terminated polymer, e.g. Polycarbonate-based diol MDI terminated Prepolymer, Polyether based diol HDI terminated Prepolymer, Poly(propylene glycol), tolylene 2,4-diisocyanate terminated (isocyanate~3.6 wt. %), Polycarbonate-based diol PPDI terminated Prepolymer, and Poly(1,4-butanediol)tolylene 2,4-diisocyanate terminated (1.9 wt. % isocyanate). Suitable isocyanates can be prepared by methods known to those of skill in the art and are also available from commercial sources, including, for example, ABI Chem, ABCR, A Chemtek, Akos Building Blocks, Alfa Aesar, Aurora Fine Chemicals, Bayer, CHEMOS GmbH, Chem Reagents, Chemtura, FCH Group, Fisher Scientific, Oakwood Chemical, Perstrop, Polysciences, Inc, Sigma-Aldrich, Suzhou Rovathin and SynQuest.

In one embodiment, the diisocyanate is derived from lysine. In one embodiment, the diisocyanate is lysine diisocyanate (LDI).

In one embodiment, the vinyl coupling agent is not particularly restricted and may be any compound comprising a single pendant hydroxyl or primary or secondary amine group that can react with the isocyanate group of the diisocyanate. In one embodiment, the vinyl coupling agent has a molecular weight between about 50 and about 500. The vinyl coupling agent may be, but is not limited to, a vinyl alcohol, an alkyl amine with vinyl groups, a vinyl amine, hydroxypropyl (meth)acrylate, 2,3-dihydroxypropyl (meth)acrylate, 1,4-butanediol monoacrylate, (poly)ethylene glycol mono(meth)acrylate, 3-aminopropyl vinyl ether, and 2-hydroxyethyl methacrylate (HEMA). In one embodiment, the vinyl coupling agent is 2-hydroxyethyl methacrylate (HEMA).

In one embodiment, the soft segment is derived from a polyol. In one embodiment, the polyol is an oligomeric macromolecule containing hydroxyl or amine end groups with low glass transition temperatures. In one embodiment, the polyol comprises a polyester, polyether or polycarbonate backbone.

In one embodiment, the soft segment may be derived from, although is not limited to, polyethylene oxide; polypropylene oxide; polytetramethylene oxide; polyisobutylene; polybutadienes; polyesters; polyethylene adipate; polytetramethylene adipate; polycaprolactone; polydimethylsiloxane; and polycarbonates.

In one embodiment, the soft segment is derived from a polycarbonate.

In one embodiment, the polar non-ionic macromer is a divinyl oligomer.

In one embodiment, the macromer is a reaction product of poly(hexamethylene carbonate) diol, lysine diisocyanate, and 2-hydroxyethyl methacrylate.

In one embodiment, the anionic component is not particularly restricted. In one embodiment, the anionic component has a molecular weight between about 50 and about 1000.

In one embodiment, the anionic component is a vinyl monomer with mono acid function such as methacrylic acid, vinyl phosphoric acid or the like; vinyl monomers with di-acids such as itaconic acid, maleic acid or the like; or vinyl monomers with tri-acids such as tricarballylic acid, tricarboxylic acid or the like.

In one embodiment, the anionic component comprises a methacrylic acid derivative; 2-(methacryloyloxy)ethyl phosphate; styrene sulphonic acid; 2(methacryloyloxy)ethyl succinate, [3-(methacryloylamino)propyl]trimethyl ammonium chloride; or 2-(methacryloyloxy)ethyl]trimethylammonium methyl chloride. In one embodiment, the methacrylic acid derivative is an amino-acid derivative. In one embodiment, the anionic component is methacrylic acid.

In one embodiment, the hydrophobic component is not particularly restricted. In one embodiment, the hydrophobic component has a molecular weight between about 50 and about 1000.

In one embodiment, component (c) is considered to be hydrophobic if when its constituent monomers are polymerized on their own, in the absence of other monomers or additives, it yields an advancing water contact angle measure of greater than about 50, 55, 60 or 65 degrees. In one embodiment, the advancing water contact angle measure is greater than about 65 degrees. Example methods of measuring water contact angle are provided in the Examples.

In one embodiment, the hydrophobic compound is a non-aromatic.

In one embodiment, the hydrophobic compound does not include a pendant halogen group, e.g. fluorine.

In one embodiment, the hydrophobic component is an alkyl methacrylate, wherein the alkyl chain is linear or branched, saturated or unsaturated, and wherein the number of carbons is less than 12. In one embodiment, the alkyl chain is non-aromatic. In one embodiment, the hydrophobic component is methyl, propyl, butyl, iso-butyl or t-butyl methacrylate. In one embodiment, the hydrophobic component is methyl methacrylate.

In one embodiment, the hydrophobic compound comprises an aliphatic alkyl side chain.

As discussed above, protein adsorption occurs immediately following the implantation of a biomaterial, or contact of body fluids such as blood to a biomaterial. This adsorbed protein layer is composed of bioactive agents that can greatly influence the behavior of cells or other body fluid elements involved in the inflammatory, immune, and foreign body responses. While the adsorbed protein layer interacts with the surface of the biomaterial, the bulk of the material does not interface with biological tissue and so may not be a major determinant in regulating protein adsorption and the subsequent inflammatory response. For this reason, biomaterials, and particularly polymeric biomaterials, can be modified in the bulk phase by the addition of components that can provide stability or mechanical integrity to the material without influencing the implant's interactions with the proteins, cells, and tissue. For polymeric materials these additives include, but are not limited to, antioxidants, fillers, cross-linkers, plasticizers, nucleating agents, and pigments. Accordingly, in one embodiment, the polymeric material further includes one or more additives, which in one embodiment, may be selected from antioxidants, fillers, cross-linkers, plasticizers, nucleating agents, and pigments.

In various embodiments, these additives may be present in an amount of less than 50, less than 40, less than 30, less than 20, less than 10, less than 5 or less than 1 percent by weight of the polymeric material.

In one embodiment, a therapeutic agent may be added to the material in the bulk phase.

In one embodiment, the therapeutic agent may be present in any amount of less than 50, less than 40, less than 30, less than 20, less than 10, less than 5 or less than 1 percent by weight of the polymeric material.

In one aspect, there are no restrictions on the manner in which the reagents are added to each other to form biocompatible polymeric materials disclosed herein, the temperature, pressure or atmosphere under which the biomaterials are synthesized from the monomer and macromers or the use of the catalysts in the reaction.

In other embodiments, there is provided methods of manufacturing a D-PHI or nD-PHI biomaterial that exhibits reduced Fab exposure, reduced monocyte adherence and/or reduced monocyte activation comprising reacting a polar non-ionic macromer, a hydrophobic component and an anionic component in the proportions described above. The method may further include preparing the macromer.

In one embodiment, the biomaterial of the present invention is prepared as described by Sharifpoor et al. S. Sharifpoor, R. Labow and J. P. Santerre, "Synthesis and Characterization of Degradable Polar Hydrophobic Ionic Polyurethane Scaffolds for Vascular Tissue Engineering Applications," *Biomacromolecules*, vol. 10, no. 10, pp. 2729-2739, 2009, the contents of which is incorporated by reference in its entirety.

In the presence of a catalyst, polar non-ionic macromonomer polyurethanes are created in a nucleophilic addition reaction between an isocyanate and molecules containing hydroxyl (a polyol) or amine functional groups to create a urethane or carbamate linkage. For the purposes of the polar non-ionic macromonomer polyurethane synthesis, the isocyanate is a low molecular weight compound that must contain at least two isocyanate groups (a diisocyanate). Polyols are oligomeric macromolecules containing hydroxyl or amine end groups with low glass transition temperatures. A variety of isocyanates and polyols, each possessing unique functionalities and properties, can be used in the synthesis of polyurethanes. In the polar hydrophobic ionic polymeric materials described herein, vinyl coupling agents are also used, which function to enhance microphase separation of the hard and soft segments.

The synthesis of polar non-ionic macromonomer polyurethane can be completed in one or two steps. The one-step process involves a simultaneous reaction of the isocyanate, polyol, and vinyl coupling agent. In the two-step prepolymer process, an excess of diisocyanate is reacted with the polyol to form NCO-terminated prepolymers with isocyanate functionality as an intermediate; this intermediate is then reacted with the vinyl coupling agent to create the final polar non-ionic macromonomer polyurethane. The reaction steps of one embodiment are illustrated in FIG. 1. The separation of the process into two steps enables a greater degree of control over the polar non-ionic macromonomer polyurethane structure and consequently, its properties.

The synthesis of polymer non-ionic macromonomer polyurethanes is also dependent upon a catalyst, the selection of which depends on the final profile of the polyurethane (gel, foam, adhesive, fiber) and its curing requirements. The two types of catalysts that can be used are metal complexes and amine compounds. Tin catalysts are effective in catalyzing the gelling reaction in which the polyol reacts with the isocyanate (and the vinyl coupling agent).

Synthesis processes will generally employ initiators and retarders. In one embodiment, the initiator used is not particularly restricted and will be within the purview of a person skilled in the art. Suitable initiators can be selected e.g. from diacyl peroxides, peroxy esters, dialkyl peroxides, dialkyl peroxydicarbonates, tert-alkylhydroperoxides, and ketone peroxides. Suitable free radical initiators include e.g. dibenzoyl peroxide, diisobutyrul peroxide, t-butyl peracetate, dicumyl peroxide, di-sec-butyperoxydicarbonate, methyl ethyl ketone peroxide, benzoyl peroxide (BPO) (available through Aldrich Chemical Co., Milwaukee, Wis.) and 1,1'-azobis(cyclohexanecarbonitrile). Light curing systems may be used to polymerize the vinyl resins, including but not limited to photopolymerizations initiated with camphorquinone (CQ, initiator) and 2-(dimethylamino) ethyl methacrylate (DMAEM, co-initiator).

Parameter variations provide the controllable aspect in polyurethane synthesis, which can include modifications to the reacting molecules (e.g. chemical composition, molecular weight, symmetry), the processing conditions (e.g. introduction of water, removal of carbon dioxide, active hydrogens), or addition of additives.

The segmented block copolymer character of polyurethanes provides freedom in designing different types of polyurethanes with a wide range of physical and chemical traits that can be specifically tailored to particular applications. The mechanical properties, specific biocompatibility, and tunable biodegradability also make them particularly suitable for use as biomaterials. Coupled with the versatility in their design, polyurethane scaffolds are an attractive alternative to the well-established PLGA scaffolds for tissue engineering applications and drug delivery systems.

In one embodiment, the form of the biomaterial of the present invention is not particularly restricted.

The variety of synthesis options and their permutations allows polyurethanes to be processed into many different forms, which include films, coatings, gels, foams, fibers, elastomers, rigid plastics, resins, adhesives, particulates or even injectable forms that cure in situ.

In one embodiment, in the case of a formed object, the biocompatible polymer material disclosed herein may be present at a surface of the object. Because, as discussed above, the adsorbed protein layer will interact with the surface of the biomaterial, the bulk of the object may comprise a suitable filler.

In various embodiments, such fillers may comprise more than 40, 50, 60, 70, 80 or 90% by weight of the object.

In one embodiment, the polymeric material may be curable.

In one embodiment, the biomaterials can include, but are not limited to a film, a gel, a foam, or a particulate.

Various methods can be employed in preparing scaffolds according to embodiments of the present invention, including nanofiber-self assembly, textile technologies, solvent casting & particulate leaching (SCPL), gas foaming, emulsification/freeze-drying, thermally induced phase separation (TIPS), electrospinning and CAD/CAM technologies, each of which is briefly described below.

Nanofiber Self-Assembly: Molecular self-assembly enables the synthesis of biomaterials with properties similar in scale and chemistry to that of the natural in vivo extracellular matrix (ECM). Moreover, these hydrogel scaffolds have shown superiority in in vivo toxicology and biocompatibility compared to traditional macroscaffolds and animal-derived materials.

Textile technologies: These techniques include all the approaches that have been successfully employed for the preparation of non-woven meshes of different polymers. In particular, non-woven polyglycolide structures have been tested for tissue engineering applications: such fibrous structures have been found useful to grow different types of cells.

Solvent Casting & Particulate Leaching (SCPL): This approach allows for the preparation of porous structures with regular porosity, but with a limited thickness. First, the polymer is dissolved into a suitable organic solvent, then the solution is cast into a mold filled with porogen particles. Such porogen can be an inorganic salt like sodium chloride, crystals of saccharose, gelatin spheres or paraffin spheres. The size of the porogen particles will affect the size of the scaffold pores, while the polymer to porogen ratio is directly correlated to the amount of porosity of the final structure. After the polymer solution has been cast the solvent is allowed to fully evaporate, then the composite structure in the mold is immersed in a bath of a liquid suitable for dissolving the porogen: water in the case of sodium chloride, saccharose and gelatin or an aliphatic solvent like hexane for use with paraffin. Once the porogen has been fully dissolved, a porous structure is obtained.

Gas Foaming: To overcome the need to use organic solvents and solid porogens, a technique using gas as a porogen has been developed. First, disc-shaped structures made of the desired polymer are prepared by means of compression molding using a heated mold. The discs are then placed in a chamber where they are exposed to high pressure $CO_2$ for several days. The pressure inside the chamber is gradually restored to atmospheric levels. During this procedure the pores are formed by the carbon dioxide molecules that abandon the polymer, resulting in a sponge-like structure.

Emulsification/Freeze-drying: This technique does not require the use of a solid porogen like SCPL. First, a synthetic polymer is dissolved into a suitable solvent then water is added to the polymeric solution and the two liquids are mixed in order to obtain an emulsion. Before the two phases can separate, the emulsion is cast into a mold and quickly frozen by means of immersion into liquid nitrogen. The frozen emulsion is subsequently freeze-dried to remove the dispersed water and the solvent, thus leaving a solidified, porous polymeric structure. While emulsification and freeze-drying allow for a faster preparation when compared to SCPL (since it does not require a time consuming leaching step), it does require the use of solvents. Moreover, pore size is relatively small and porosity is often irregular. Freeze-drying by itself is also a commonly employed technique for the fabrication of scaffolds.

Thermally Induced Phase Separation (TIPS): Similar to emulsification/freeze-drying, TIPS requires the use of a solvent with a low melting point that is easy to sublime. For example dioxane could be used to dissolve polylactic acid, then phase separation is induced through the addition of a small quantity of water: a polymer-rich and a polymer-poor phase are formed. Following cooling below the solvent melting point and some days of vacuum-drying to sublime the solvent, a porous scaffold is obtained.

Electrospinning: A highly versatile technique that can be used to produce continuous fibers from submicrometer to nanometer diameters. In a typical electrospinning set-up, a solution is fed through a spinneret and a high voltage is applied to the tip. The buildup of electrostatic repulsion within the charged solution, causes it to eject a thin fibrous stream. A mounted collector plate or rod with an opposite or grounded charge draws in the continuous fibers, which arrive to form a highly porous network. The primary advantages of this technique are its simplicity and ease of variation. At a laboratory level, a typical electrospinning set-up only requires a high voltage power supply (up to 30 kV), a syringe, a flat tip needle and a conducting collector. By modifying variables such as the distance to collector, magnitude of applied voltage, or solution flow rate, researchers can dramatically change the overall scaffold architecture.

CAD/CAM Technologies: Because most of the above techniques are limited when it comes to the control of porosity and pore size, computer assisted design and manufacturing techniques have been introduced to tissue engineering. First, a three-dimensional structure is designed using CAD software. The porosity can be tailored using algorithms within the software. The scaffold is then realized by using ink-jet printing of polymer powders or through Fused Deposition Modeling of a polymer melt.

The biomaterials as described herein have the advantage of being synthetic. Such materials have the advantage of improved reproducibility relative to natural biomaterials such as glycosaminoglycans or collagen, which in turn is associated with more reliable performance and functionality. Polyurethane based biomaterials also have the advantage of better raw material availability as compared to these natural materials.

In accordance with one aspect of the present invention, polyurethanes undergo biodegradation in vivo due to their chemical composition and the presence of hydrolytic esterases in the body and their biodegradation tendencies can be exploited to design specific biodegradation profiles. Suitably, monomers and other degradation byproducts can be selected such that they are not cytotoxic. For example, the monomers of the polyurethane materials can be selected to dilute or eliminate the pro-inflammatory nature of acid by-products such as lactic acid, generated from polylactic glycolic acid (PLGA) biomaterials.

Modulus and stiffness of the D-PHI material will affect in vivo performance. Depending on the particular application, it may be advantageous to have a material to match the natural stiffness of the particular tissue or environment to properly direct cell behavior or withstand in vivo loading conditions. The varied mechanical properties of D-PHI allow for this flexibility. In one embodiment, the use of materials and devices as described herein is not particularly restricted and the materials and devices can be used in various applications to repair or augment parts or functions of the body. Such materials and devices can be used for a variety of purposes relating to orthopedic, cardiovascular, ophthalmic, dental, and wound-healing applications.

Examples of biomedical articles that can be formed in whole or in part using polar hydrophobic ionic polymeric materials and, in particular, polar hydrophobic ionic polyurethanes as described herein include: cardiac assist devices, tissue engineering polymeric scaffolds and related devices, cardiac replacement devices, cardiac septal patches, wound dressings, intra aortic balloons, percutaneous cardiac assist devices, extra-corporeal circuits, A-V fistual, dialysis components (tubing, filters, membranes, etc.), aphoresis units, membrane oxygenator, cardiac by-pass components (tubing, filters, etc.), pericardial sacs, contact lenses, cochlear ear implants, sutures, sewing rings, cannulas, contraceptives, syringes, o-rings, bladders, penile implants, drug delivery systems, drainage tubes, pacemaker lead insulators, heart valves, blood bags, coatings for implantable wires, catheters, vascular stents, angioplasty balloons and devices, bandages, heart massage cups, tracheal tubes, mammary implant coatings, artificial ducts, craniofacial and maxillofacial reconstruction applications, ligaments, fallopian tubes, biosensors and bio-diagnostic substrates.

Non-biomedical articles that can be fabricated in whole or in part using polymeric materials as described herein include, for example, extruded health care products, bioreactor catalysis beds or affinity chromatography column packings, or a biosensor and bio-diagnostic substrates. Non-medical applications include fibre membranes for water purification and varnishes with anti-microbial function for aseptic surfaces.

All documents referenced herein are incorporated by reference, however, it should be appreciated that any patent, publication, or other disclosure material, in whole or in part, that is incorporated by reference herein is incorporated only to the extent that the incorporated material does not conflict with definitions, statements, or other disclosure material set forth in this disclosure. As such, and to the extent necessary, the disclosure as explicitly set forth herein supersedes any conflicting material incorporated herein by reference.

The above description, the examples below and accompanying drawings should be taken as illustrative of the invention, and are intended to cover any variations, uses, or adaptations of the invention following, in general, the principles of the invention and including such departures from the present disclosure as come within known or customary practice within the art to which the invention pertains. The scope of the invention is therefore intended to be limited solely by the scope of the appended claims.

EXAMPLES

Example 1 D-PHI Synthesis 1.1 D-PHI Film Synthesis

As described by Sharifpoor et al. S. Sharifpoor, R. Labow and J. P. Santerre, "Synthesis and Characterization of Degradable Polar Hydrophobic Ionic Polyurethane Scaffolds for Vascular Tissue Engineering Applications," *Biomacromolecules*, vol. 10, no. 10, pp. 2729-2739, 2009, the contents of which is incorporated by reference in its entirety. D-PHI films were synthesized by reacting a divinyl oligomer (DVO) with methacrylic acid (MAA, Sigma-Aldrich) and methyl methacrylate (MMA, Sigma) in varying molar ratios as summarized in Table 1. The selected film formulations were created to intentionally increase and decrease the hydrophobic and ionic content as provided by the MMA and MAA monomers, respectively. The benzoyl peroxide (BPO, Sigma) was added in a 0.0032 mol/mol vinyl group ratio. The mixture was then stirred for a minimum of 20 hours at room temperature in a light-protected environment. 50 µL of each mixture was pipetted into each well of a polypropylene 96-well plate (Costar) using a calibrated micropipette. The plate was then sealed and cured in a vacuum oven purged with nitrogen at 110° C. for 24 hours.

TABLE 1

DVO:MAA:MMA monomer ratios used in D-PHI film formulations.

| Film Formulation | DVO:MAA:MMA |
|---|---|
| D-PHI 1:5:15 | 1:5:15 |
| D-PHI 1:20:39 | 1:20:39 |
| D-PHI 1:2:24 | 1:2:24 |
| D-PHI 1:10:10 | 1:10:10 |
| D-PHI 1:1:7 | 1:1:7 |

1.2 D-PHI Scaffold Synthesis

D-PHI porous scaffolds were prepared as described by Sharifpoor et al. Briefly, a mixture of DVO, MAA, and MMA in molar ratios of 1:5:15 and 1:1:7 were prepared. Polyethylene glycol (PEG) in a 10% wt relative to the mixture and a BPO initiator were added and mixed overnight (room temperature, light protected). The following day, NaHCO$_3$ particles were added in a 65 wt % relative to the resin. The mixture was stirred for 12 hours (room temperature, light protected) and loaded into Teflon molds to cure at 110° C. for 24 hours. The cured scaffolds underwent a 14-day salt leaching process in distilled and deionized water that was replaced daily. The scaffolds were sonicated for 2 hours/day.

Example 2 Protein Analysis

2.1 Adsorbed IgG Fab Quantification

An enzyme linked immunosorbent assay (ELISA) was used to quantify Fab exposure from adsorbed IgG on D-PHI films and TCPS surfaces. The amount of Fab exposed is significant as its presence can influence the adhesion and activation of monocytes, other cells and proteins associated with coagulation and complement proteins. D-PHI films in the 96-well plates and TCPS were sterilized in 70% ethanol for 24 hours and dried in a laminar flow hood. The films were hydrated and incubated with 200 μL of 1% penicillin-streptomycin (PenStrep) in phosphate buffered saline (PBS) for a minimum of 24 hours. Each of the five D-PHI film formulations were then coated with 100 μL of sterile filtered IgG (Jackson Immuno Research ChromPure Human IgG) solution diluted to a concentration of 200 μg/mL in Roswell Park Memorial Institute-1640 media (RPMI-1640) for 24 hours at 37° C. An equal number of D-PHI formulation (DVO:MAA:MMA ratio of 1:5:15) were incubated with RPMI-1640. The following day, the films were washed 2× with 200 μL of PBS and incubated with 100 μL of a secondary antibody, horseradish peroxidase (HRP) conjugated Fab-specific anti-human IgG in a ratio of 1:32000 diluted in PBS for 1 hour at room temperature. Samples were washed 3× with 400 μL of a 0.05% Tween in PBS wash buffer. Films were transferred to a new TCPS plate to ensure only the IgG adsorbed to the films and not the plate wells would be quantified. The samples were incubated with 100 μL of a tetramethyl benzidine (TMB) substrate solution for 25 minutes. The substrate solution was then transferred into a new well to which a 50 μL stop solution of 2 N sulphuric acid was applied. The absorbance of the solutions was read with an ERSA Max microplate reader at 450 nm with a correction wavelength of 570 nm.

2.2 Adsorbed Protein Quantification

A bicinchoninic acid (BCA) assay (Pierce Scientific) was used to quantify total adsorbed protein on D-PHI films to ensure differences in Fab exposure were not due to differences in total adsorbed IgG. D-PHI films were sterilized, dried, incubated in 1% PenStrep, and coated with IgG as per the steps in 2.1. Control films were also prepared using RPMI-1640 in place of the IgG solution. Samples were then incubated with 200 μL of 2% sodium dodecyl sulfate (SDS) in distilled water for 24 hours at room temperature. A BCA assay was performed according to the manufacturer's protocol.

Quantification of IgG Fab can be used as an indicator of immune cell activation. As observed in FIG. 2, the exposed Fab was significantly greater on TCPS ($p<0.05$) than that of all D-PHI film formulations. D-PHI 1:1:7 films supported greater adsorbed IgG Fab exposure compared to the D-PHI 1:5:15 films ($p<0.0005$), and the other D-PHI films which had molar ratios of macromonomer:monomer of 1:>20 which were even less than that of the D-PHI-1:5:15 (1.0:5.0:15.0). Total protein adsorbed to the D-PHI films was quantified to ensure the differences in IgG Fab across the films were not due to differences in total IgG adsorbed. Because all formulations supported the same level of total IgG adsorption, differences in Fab exposure could not be attributed to differences in total IgG present.

Example 3 D-PHI Characterization

Figure 2:
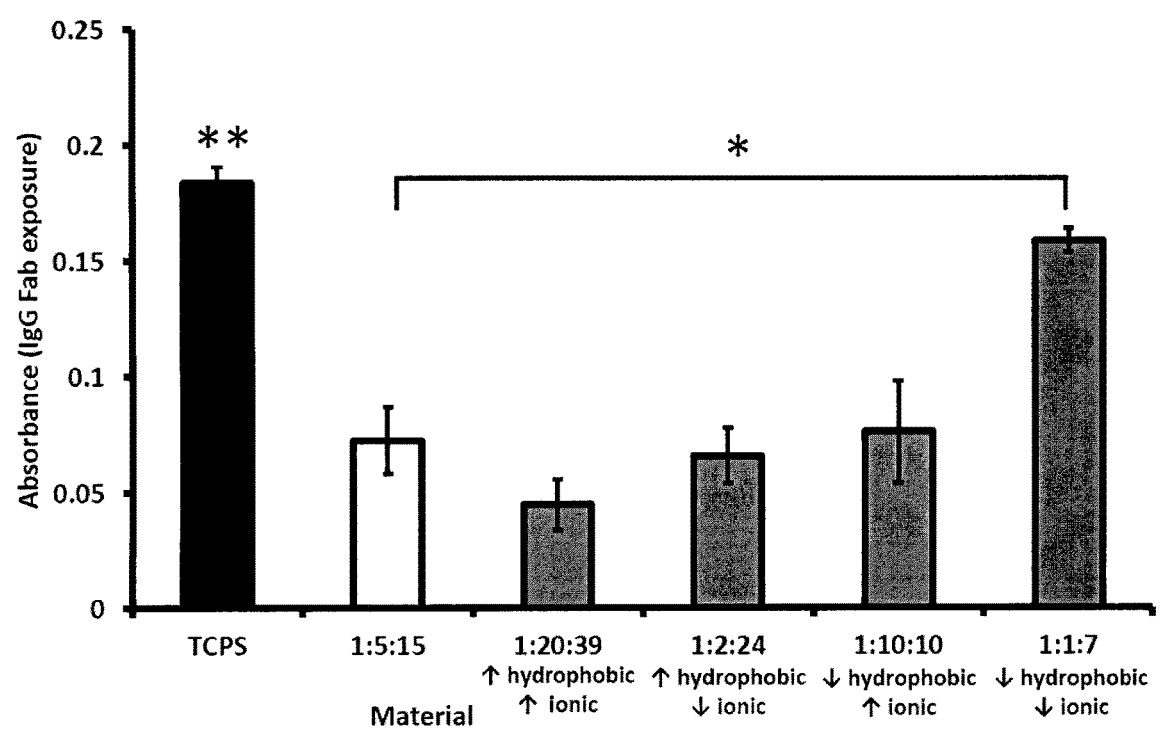
Figure 3:
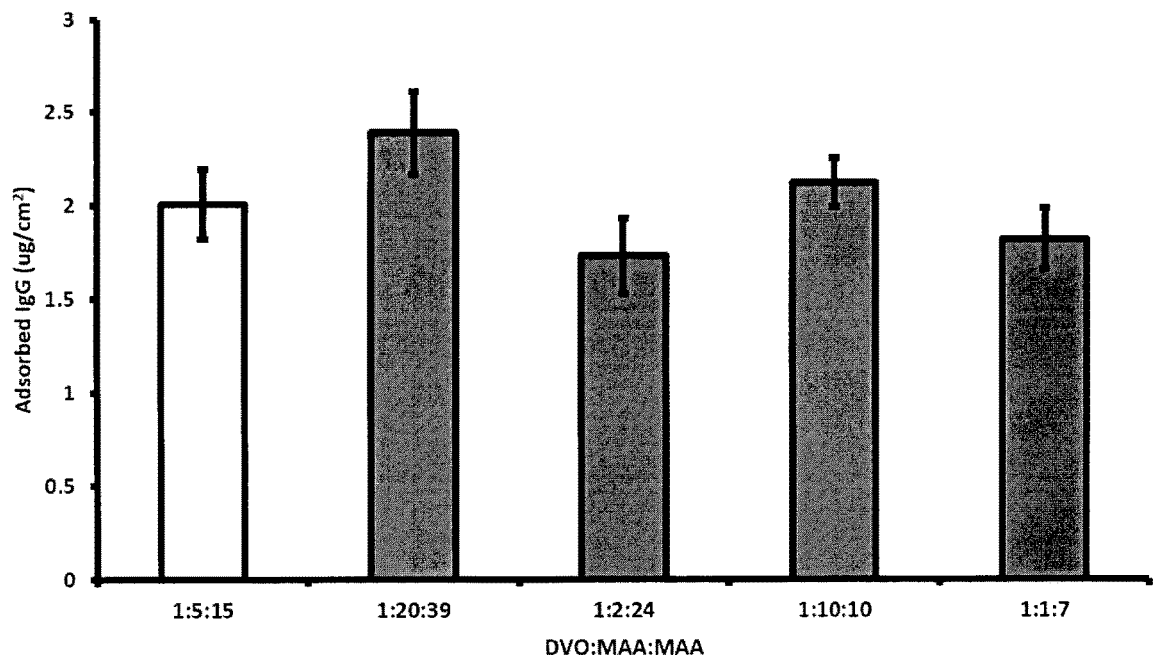

The characterization methods listed below were performed with the D-PHI-1:5:15 formulation and the low hydrophobic, low ionic formulation (D-PHI 1:1:7) since it showed a statistically significant increase in IgG Fab exposure compared to the D-PHI-1:5:15 film (see FIG. 2).

3.1 X-Ray Photoelectron Spectroscopy (XPS)

XPS analysis was performed using a Thermo Scientific K-Alpha XPS system located at Surface Interface Ontario, University of Toronto. High and low resolution analysis was obtained with a 90° takeoff angle. The percent atomic composition was determined by low resolution analysis of carbon, oxygen, and nitrogen. The percent atomic composition of the various carbon bonds was determined using high resolution analysis.

The surface functional groups (Table 2) vary between the D-PHI films and TCPS. The chemistry of D-PHI involves a greater variety of surface bonds [see K. Battiston, R. Labow and P. Santerre, "Protein binding mediation of biomaterial-dependent monocyte activation on a degradable polar hydrophobic ionic polyurethane," *Biomaterials*, vol. 33, pp. 8316-8328, 2012, the contents of which is incorporated herein by reference in its entirety.]. This reflects the inherent differences in their material chemistries, which may contribute to differences in IgG Fab exposure quantified between the films and TCPS. One specific example is the carboxyl functional group, which has a much smaller atomic percentage on TCPS ($16.80\pm0.05\%$ for TCPS vs. $30.22\pm1.60\%$ for D-PHI-1:5:15 and $28.50\pm3.53$ for D-PHI 1:1:7, $p<0.01$). This may support the idea that decreased ionic content does in fact result in increased IgG Fab exposure (as it relates to FIG. 2), which is consistent with the findings for Fab on D-PHI 1:1:7. Likewise, the virtual absence of polar non-ionic groups in TCPS is associated with elevated IgG Fab presentation, as per FIG. 2. The differences in surface ionic content for different D-PHI materials leads to differences in Fab expression (FIG. 2.)

TABLE 2

High resolution XPS data for the types of carbon bonds present at the surface of D-PHI 1:5:15 and D-PHI 1:1:7. n = 3.

| Functional group(s) | TCPS (Atomic % ± SE) | D-PHI-1:5:15 (Atomic % ± SE) | D-PHI 1:1:7 (Atomic % ± SE) |
|---|---|---|---|
| —CH (285 eV) | 60.28 ± 0.24 | 57.39 ± 2.08 | 62.50 ± 5.63 |
| —COOH or CO(O—) (287 eV) | 16.80 ± 0.05** | 30.22 ± 1.60 | 28.50 ± 3.35 |
| O=C(O—)$_2$ (289 eV) | N/A | 6.37 ± 0.98* | 2.51 ± 0.45* |
| O=C(O—)(N—)) (290 eV) | N/A | 6.02 ± 0.26 | 6.49 ± 1.89 |

*$p = 0.05$ between D-PHI formulations.
**$p < 0.01$ between TCPS and D-PHI films.

3.2 Contact Angle

Advancing water contact angle measurements were obtained using a goniometer (NRL C.A., Ramé-Hart, Inc, Mountain Lakes, N) for each D-PHI film formulation. A microsyringe was used to place a 20 µL droplet of distilled/ deionized water on the films. The contact angles on either side of the droplet were measured and averaged. Advancing contact angle measurements show a statistically significant but very small decrease in hydrophobicity for D-PHI 1:1:7 as indicated by a smaller contact angle (p<0.001), as shown in Table 3. In contrast to what would have been predicted by the observation that the control has more ionic content (i.e. higher ionic monomer), the contact angle for the control is marginally higher than the material with least ionic monomer. These data show that the specificity of interactions with IgG that is shown in FIG. 2 only shows subtle differences using classical surface analysis methods such as contact angle, as there is no significant difference between the high Fab and D-PHI-1:5:15 substrate.

TABLE 3

Advancing contact angle measurements for D-PHI 1:5:15 and D-PHI 1:1:7 film. n = 10.

| DVO:MAA:MAA* | Average Contact Angle (°) ± Standard Error |
|---|---|
| 1:5:15 | 81.4 ± 1.4 |
| 1:1:7 | 77.8 ± 2.9 |

*p < 0.001 between D-PHI film formulations.

3.3 Swelling Studies of D-PHI Films and Scaffolds

Swelling studies should be a reflection of the propensity for water to interact with a material. Protein may be influenced by such interactions. If the water absorption is tight and allows little interchange between the water and proteins at the surface then protein interaction with the surface may be minimized. Gravimetric analysis was used to measure swelling in aqueous environments. Following immersion and drying of D-PHI films and scaffolds in 70% ethanol, samples were immersed in 90% and 100% ethanol for 1 hour each. The samples were then incubated in Dulbecco's modified Eagle's medium (DMEM) for 5 days at 37° C. Samples were weighed using a Fischer Scientific Mettler AT201 scale before and after media immersion to determine the percent change in weight. Samples were lightly blotted to remove non-absorbed media before the final weigh in.

Swelling studies can also be used as an indication of the hydrophobic/hydrophilic character of materials [see P. Sinko and A. Martin, Martin's *Physical Pharmacy and Pharmaceutical Sciences*, New York: Lippincott Williams & Wilkins, 2006.]. In swelling studies of both D-PHI films and scaffolds (Table 4 and Table 5), D-PHI 1:1:7 had a lower degree of swelling than the D-PHI-1:5:15 after submersion in aqueous media (4.07±0.65% vs. 11.72±1.36% in films and 97.12±13.36% vs. 179.95±29.85% in scaffolds, p<0.0001), respectively. Hence, the differential in water uptake was more sensitive to materials differences than was the contact angle and XPS data.

TABLE 4

Swelling studies with D-PHI films. n = 5.

| DVO:MAA:MAA* | Weight Change ± Standard Error (Wt %) |
|---|---|
| 1:5:15 | 11.72 ± 1.36 |
| 1:1:7 | 4.07 ± 0.65 |

*p < 0.0001 between formulations.

TABLE 5

Swelling studies with D-PHI scaffolds. n = 20.

| DVO:MAA:MAA* | Weight Change ± Standard Error (Wt %) |
|---|---|
| 1:5:15 | 179.95 ± 29.85 |
| 1:1:7 | 97.12 ± 13.36 |

*p < 0.0001 between formulations.

As noted, swelling is dependent on the hydrophobic/ hydrophilic functionalities of the material. Hydrophilic materials are more susceptible to forming hydrogen bonds with the water molecules of the aqueous media, which leads to a greater degree of swelling [see Sinko P. et al.]. MMA provides the hydrophobic character of D-PHI and the lowered hydrophobic content of D-PHI 1:1:7, which was also established by contact angle measurements, would predict a higher degree of swelling. However, swelling is also influenced by the material's ionic character, which affects the material's propensity to take up water. A decreased ionic content afforded to D-PHI 1:1:7 by the decreased MAA content may have contributed to the overall lower degree of swelling compared to D-PHI 1:5:15. It would not be obvious which of these two features would be dominant, particularly since there were three times more hydrophobic monomer over that of ionic monomer.

Swelling studies are useful in observing material behavior in a wet environment, which more closely reflects an aqueous in vivo environment. Overall greater swelling was observed in D-PHI scaffolds over D-PHI films. This can be attributed to the porous nature of the scaffolds, which provides more surface area for interactions with the aqueous media.

3.4 Mechanical Properties

These data generally show that a range of mechanical properties can be obtained by varying the monomer ratios of the D-PHI family and that materials of interest have properties that are competitive with that of classical polyurethanes, thereby making the uniquely favored IgG Fab materials practical in terms of medical applications requiring a range of physical properties.

D-PHI films were created as described in Example 1 but cured in rectangular Teflon molds. They were cut into dumbbell-shaped pieces with a thickness of 1-2 mm, gauge length of 3.5 mm, and width of 2 mm along the gauge length. The film widened to 10 mm at the edges. The films were sterilized overnight in 70% ethanol, followed by submersion in 90% and 100% ethanol for 1 hour each. After the films were dried, they were incubated for 5 days at 37° C. in PBS. The films were then subjected to tensile mechanical testing using an Instron uniaxial servohydraulic testing machine (Instron model 4501) equipped with a 1000 N tension-compression load cell and operated at a cross height speed of 5 mm/min. Stress-strain data was collected from 10 dumbbell-shaped samples of the D-PHI-1:5:15 and D-PHI 1:1:7 films, from which the elastic modulus and elongation were determined.

The D-PHI 1:5:15 and D-PHI 1:1:7 formulation of D-PHI films exhibited dissimilar mechanical properties under tensile testing. The elastic modulus and elongation at break (see FIG. 4) were determined for each formulation. Mechanical tests were performed in wet conditions (after films were soaked for 5 days in PBS) for a more similar representation of the in vivo environment.

A greater degree of swelling has been linked to poorer mechanical properties due to the disruption of the material's atomic structure by interacting water molecules, but the D-PHI-1:5:15 film had a much greater modulus than D-PHI 1:1:7 (105.23±24.37 MPa vs. 8.15±1.17 MPa respectively, p<0.00001).

A homopolymer of MMA, poly(methyl methacrylate) (PMMA), has a modulus ranging from 1800-3100 MPa and a homopolymer of MAA, poly(methacrylic acid), has a modulus of about 360 MPa. These moduli are all greater than that of D-PHI 1:5:15 and D-PHI 1:1:7 films. Extrapolating from this data, it is possible that MMA and MAA contribute in making the D-PHI-1:5:15 stiffer than the D-PHI 1:1:7.

Figure 4:
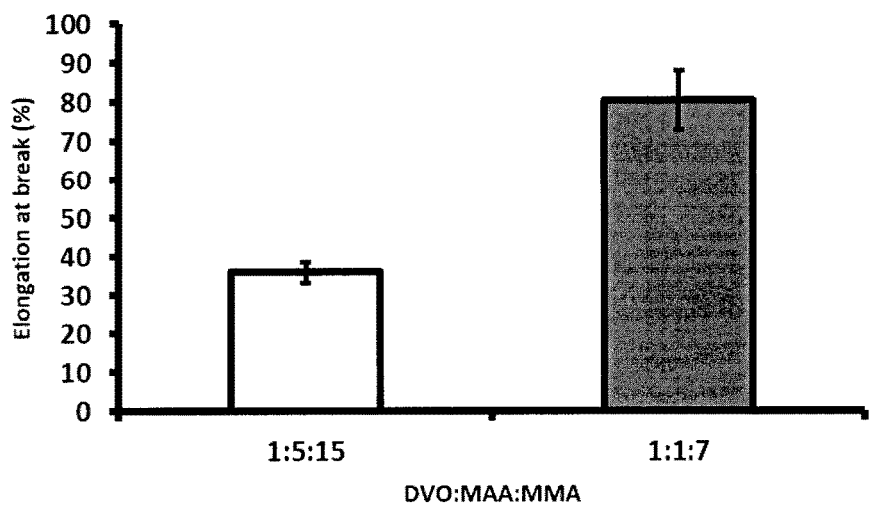

D-PHI 1:1:7 also exhibited greater elongation properties, as can be observed in FIG. 4: the elongation of D-PHI 1:1:7 at rupture is more than twice that of the D-PHI 1:5:15 formulation (80.33±24.03% vs. 35.88±8.07% respectively). In addition, the representative stress-strain curves show different D-PHI film behaviors under stress. The D-PHI 1:5:15 film exhibits the stress-strain behavior of ductile materials in which there is a relatively linear increase in the elastic region until the yield point, after which strain hardening occurs until the ultimate tensile strength is reached (at break). In contrast, the stress-strain curve of D-PHI 1:1:7 is more similar to that of an elastomer with a smoother increase of stress with increasing strain. D-PHI films are polyurethanes, which are known for their copolymer structure that characteristically contain both hard and soft segments; the ratio of the hard and soft segments impart the polyurethane with specific mechanical properties. Generally, a greater proportion of soft segments will lower tensile strength and modulus, and increase elongation at break while a greater proportion of hard segments will increase tensile strength and modulus, and decrease elongation at break. The hard and soft character of D-PHI is provided by LDI and PCN respectively and these ratios were not altered in creating D-PHI 1:1:7. The changes in mechanical behavior can therefore be attributed to the changes in MMA and MAA content. The effect of decreasing MMA and MAA appears to highlight the soft segment characteristic of D-PHI 1:1:7. A continuous soft phase results in characteristic elastomeric behavior in which there is no clear yield point, unlike the yield point prominently featured in the D-PHI 1:5:15 stress-strain curve.

3.5 Gel Content and Toxicity

Films were immersed in acetone for 1 day and vacuum dried. Samples were weighed (Fischer Scientific Mettler AT201 scale) before and after acetone immersion to determine the change in weight. The gel content (wt %) as described by Yang, was determined using the equation $$wt\ \% = w_t/w_0 \times 100\%$$

where $w_t$ is the weight of the dry film after immersion in acetone, and $w_0$ is the initial weight of the film.

The results of gel content studies for the D-PHI-1:5:15 and D-PHI 1:1:7 films are shown in Table 6. The gel content percentage indicates that both film formulations have high monomer conversion. Given the relationship between toxicity and residual monomers, this suggests that both the D-PHI formulations have low toxicity levels. Low toxicity is especially important when the films are used to culture monocytes or other cells in order to reduce pro-inflammatory behavior.

TABLE 6

Gel content studies with D-PHI 1:1:7 films. n = 5.

| DVO:MAA:MAA | Gel Content ± Standard Error (Wt %) |
| --- | --- |
| 1:5:15 | 99.23 ± 0.94 |
| 1:1:7 | 99.55 ± 0.47 |

Example 4 In Vitro Cell Culture Studies 4.1 Monocyte Isolation and Culture

Monocytes were isolated from the peripheral blood of healthy volunteers at Mount Sinai Hospital, Toronto, Ontario (University of Toronto ethics approval protocol #22203). Blood was layered onto Histopaque-1077 and separated by density gradient centrifugation. The buffy coat, container mononuclear cells, was collected and subjected to a series of washes. Monocytes were seeded at a concentration of 200,000 per well in 96-well plates on non-coated (NC) or IgG-coated (human IgG, Jackson ImmunoResearch) D-PHI and TCPS surfaces in RPMI-1640 medium supplemented with 10% AHS. Protein pre-coating was performed by first incubating surfaces with PBS supplemented with 1% Penicillin/Streptomycin for 24 hr, followed by a 24 hr incubation period with IgG in serum-free RPMI-1640 medium (200 µg/ml, 100 µl per well). To assess the role of the Fab domain of IgG exposed to monocytes and its impact on activation, prior to cell seeding IgG-coated surfaces were incubated with a Fab-specific IgG (20 µg/ml) for 1 hr. Blocking antibody was also supplemented into medium with each medium change (20 µg/ml). Samples were analyzed using the methods outlined in 4.2.

4.2 Cell Lysis for DNA Analysis

After 3 days, 100 µL of a lysis buffer of 0.05% Triton/EDTA in PBS was transferred into the sample wells. After placing on ice for 1 hour, the cells were mechanically disrupted and the lysate was transferred to eppendorf tubes that were kept on ice. Cells from D-PHI films were transferred after films were thoroughly scraped. A dye solution was prepared with a 1×TNE buffer (0.010 M Trizma base, 0.2 M NaCl and 0.001 M EDTA in ddH$_2$O, pH 7.4) and 0.1% Hoescht Dye #33258. In duplicate repeats, 10 µL of the cell lysate from each eppendorf was added to 100 µL of the dye solution and read against a DNA calf thymus standard using a FL600 Microplate Reader (Bio-tek) at 360/460 nm (absorption/emission). DNA mass quantification was used as a measure of monocyte number.

Figure 5:
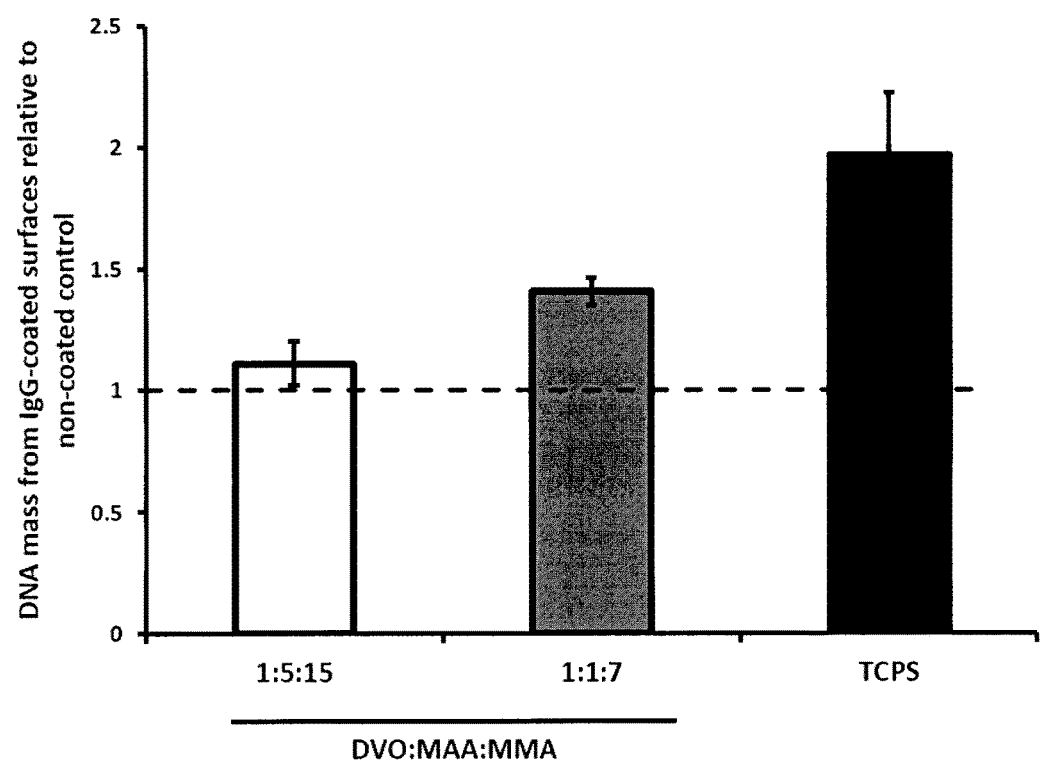

Monocyte attachment to the D-PHI 1:5:15, D-PHI 1:1:7 and TCPS surfaces were investigated and cellularity was quantified using a DNA lysis test. The values of DNA mass correlate with the number of adherent monocytes in which a greater number of adherent monocytes result in a greater quantification of DNA mass. The results, summarized in FIG. 5, confirm the findings of FIG. 2 in which an increase in exposed IgG Fab results in greater monocyte attachment. Notably, D-PHI 1:1:7 and the TCPS surfaces significantly increased monocyte attachment following IgG adsorption compared to their respective non-coated control surfaces (p<0.05, p<0.0001 respectively). This further demonstrates the correlation between IgG Fab exposure and monocyte attachment in which an increase in IgG Fab results in a greater number of adhered monocytes.

D-PHI has diverse surface functional groups, which may be distributed in such a way to stabilize the conformation of IgG and reduce its ability to activate monocytes. For example, surface patterning at the micro or nanoscale can effectively alter the distribution of functional groups, which in turn allows for specific tailoring of protein and cell activity.

D-PHI 1:1:7 and the TCPS surfaces significantly increased monocyte attachment following IgG adsorption compared to their respective non-coated control surfaces ($p<0.05$, $p<0.0001$ respectively), supporting the correlation between IgG Fab exposure and monocyte attachment in which an increase in IgG Fab results in a greater number of adhered monocytes.

In terms of normalized monocyte quantities, only TCPS differed from the D-PHI-1:5:15 film ($p<0.05$). There are greater differences in TCPS surface chemistry from D-PHI film surface chemistry compared to the differences between the D-PHI-1:5:15 and D-PHI films 1:1:7 (refer to XPS results in Table 2), which supports the view that IgG adsorption and Fab exposure are surface-dependent.

4.4 Cell Area Quantification of Adhered Monocytes

Image analysis of the SEM images was performed using ImageJ software to quantify the monocyte surface area as an indication of cell spreading and to quantify the pseudopodic area of the monocytes as an indication of cell activation. The difference in contrast between the monocytes and background on the SEM enabled identification of the cells. Monocytes could also be identified by their rather circular shape. Monocyte area was measured as described by Ross [J. Ross, *ImageJ: Introduction to Image Analysis*, Aukland: The University of Aukland, 2012.]; the process is outlined below. ImageJ application commands are shown in italics.

1. Set scale: *Analyze→Set Scale*
2. Increase differentiation between cells and background: *Image→Adjust→Brightness/Contrast*
3. Remove noise with a filter: *Process→Filters→Median*
4. Define cell boundaries: *Process→Find Edges*
5. Convert to binary image: *Image→Adjust Threshold*
6. Connect any gaps in cell boundaries and fill in any holes in cells: *Process→Binary→Close* to connect boundaries, followed by *Process→Binary→Fill Holes* (the Close operation can be decoupled by performing this step separately using *Process→Binary→Dilate*, *Process→Binary→Fill Holes*, followed by *Process→Binary→Erode* where the Dilate and Erode operations must be performed as a pair).
7. Separate any joined monocytes: *Process→Binary→Watershed*. Note that physically overlapping monocytes were excluded from analysis since they could not be accurately separated, but monocytes that merely contacted each other were included.
8. Determine monocyte area: *Analyze→Analyze Particles*

Pseudopodia are the cell extensions from the main cell body that cells such as monocytes/macrophages use for phagocytosis. These pseudopodia are smaller in nature and thinner than the main cell body and, using this assumption, simple mathematical morphological operations can be used to quantitatively measure the pseudopodic area [R. Haralick and L. Shapiro, *Computer and Robot Vision*, Addison-Wesley Publishing Company, 1992.]. This process involved a series of erosions and dilations following cell surface quantification. Through the series of erosions, the thinner pseudopodia were removed from the image, and through the series of dilations, the original area of the main monocyte body was restored. The full procedure can be found below.

1. Erode binary image from which cell surface area was quantified until pseudopodia are removed: *Process Binary→Erode as needed*
2. Dilate resulting image the same number of times it was eroded: *Process→Binary→Dilate as needed*
3. Determine non-pseudopodic monocyte area: *Analyze→Analyze Particles*

To determine the pseudopodic area, subtract the total monocyte area (obtained from previously outlined surface area measurements) with the non-pseudopodic monocyte area. The percentage contributed by the pseudopodic area to entire cell area was determined by the ratio of the pseudopodia area by the total monocyte area [T. Okagaki, B. Clark and L. Twiggs, "Measurement of Number and Cross-sectional Area of Basal Cell Pseudopodia: A New Morphometric Method," *The Journal of Cell Biology*, vol. 91, pp. 629-636, 1991.].

Figure 6:
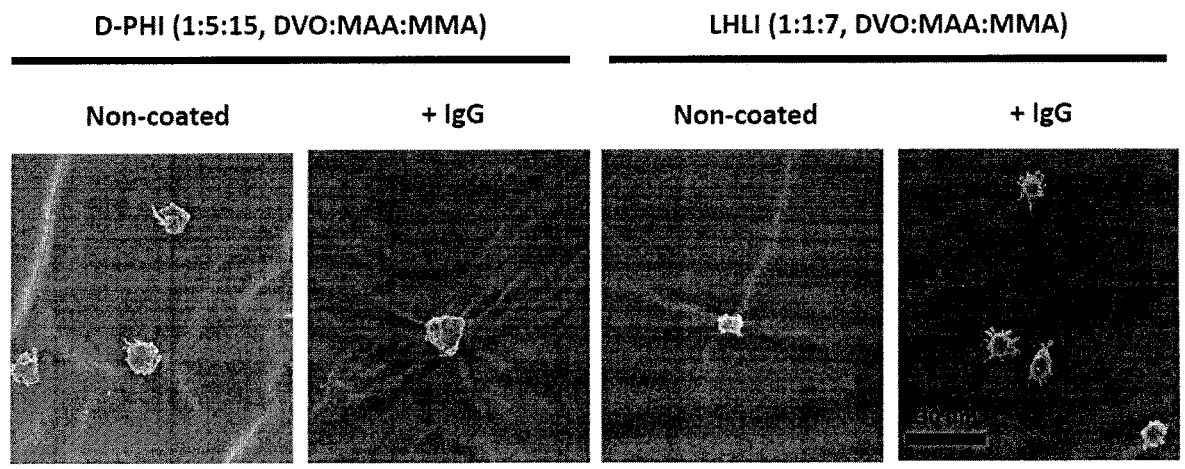
Figure 7:
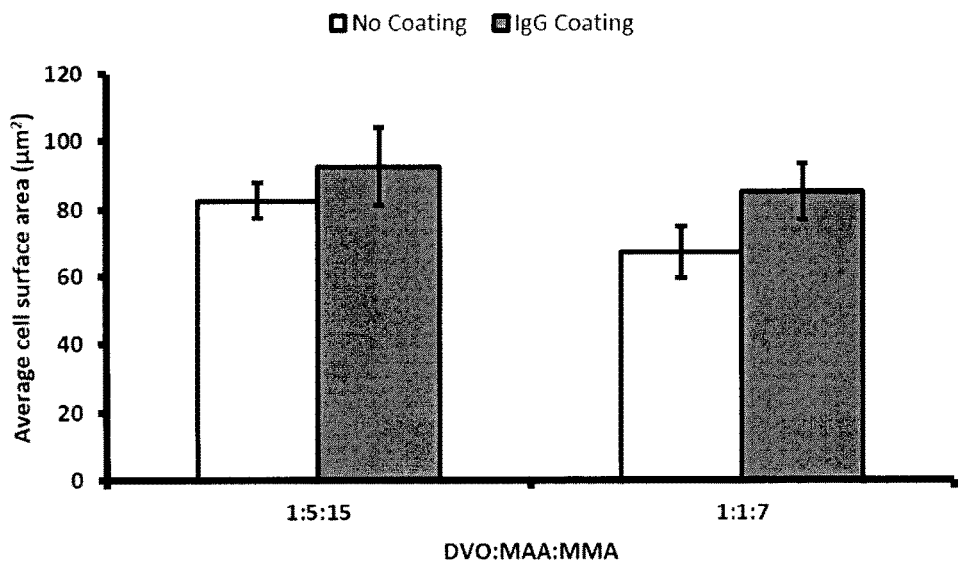
Figure 8:
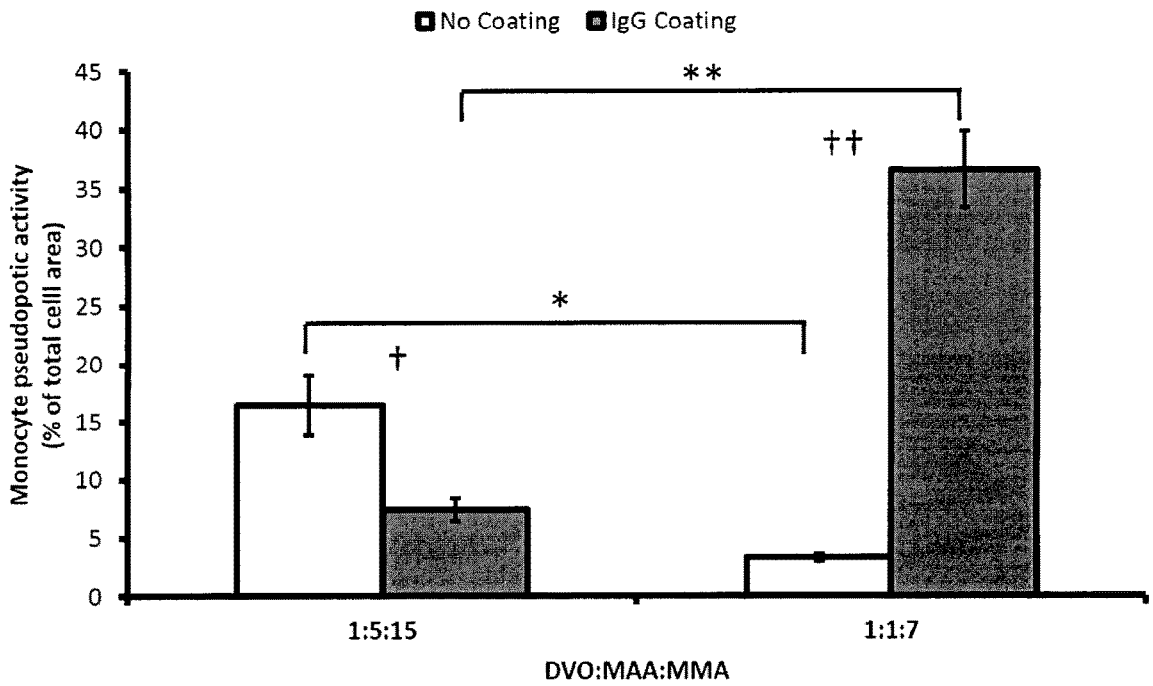

In addition to quantifying monocyte attachment, the morphology of the seeded monocytes was observed. FIG. 6 shows that the monocytes on the D-PHI 1:1:7 IgG-coated film are less spherical in shape with rougher edges and greater pseudopodic activity in comparison to the non-coated D-PHI 1:1:7 control. The irregularly shaped monocytes on the D-PHI 1:1:7 IgG-coated film are indicative of a more activated monocyte state, which is more conducive for eliciting an unfavorable immune response [see M. Shen, I. Garcia, R. Maier and T. Horbett, "Effects of adsorbed proteins and surface chemistry on foreign body giant cell formation, tumor necrosis factor alpha release and procoaguland activity of monocytes," *Journal of Biomedical Materials Research*, vol. 70, no. 4, pp. 533-541, 2004.]. Pseudopodic activity was quantified as the pseudopodic area divided by the total spread area of each cell. There is a large increase in pseudopodic area of monocytes seeded on D-PHI 1:1:7 ($p<0.00001$), which reinforces the role of D-PHI 1:1:7 in exposing more Fab sites on adsorbed IgG and consequently increasing monocyte attachment and activation.

The findings demonstrate that the D-PHI 1:1:7 IgG-coated film has a greater number of adherent monocytes and contains monocytes in a more activated state.

Example 5—Comparison of the In Vitro Dependence of the Monocytic Response on Material (TCPS Vs. D-PHI), Adsorbed Protein (IgG Vs. Fibronectin) and Serum (Autologous Human Serum Vs. Fetal Bovine Serum)

These data show the unique difference associated with immune-globulin proteins that were not universally replicated with other common adhesive proteins such as fibronectin.

5.1 Film Preparation for Cell Culture

D-PHI 1:5:15 films were synthesized as described in Example 1. Samples were prepared for cell culture and seeded with monocytes as described in Example 4.

5.2 DNA Quantification

DNA mass quantification was performed as described previously in Example 4.2.

5.3 Cytokine Analysis

TNFα and IL-10 were assayed using ELISA kits (eBioscience) according to the manufacturer's protocol. Samples were incubated overnight for increased assay sensitivity. Plates were washed four times with wash buffer (0.05% Tween 20 in PBS) between incubations using a manifold dispenser.

The results showed that monocytes secrete different cytokine profiles depending on material, adsorbed protein, and serum type.

To compare the effects of adsorbed proteins, all serum conditions (no serum, AHS, FBS) were lumped together in each of the three categories: IgG vs. fibronectin vs. no coating. This way, serum effects were marginalized out and protein effects could be isolated. From this larger dataset (n=24), the TNFα/IL-10 ratio was calculated for each sample, and averaged.

Figure 9:
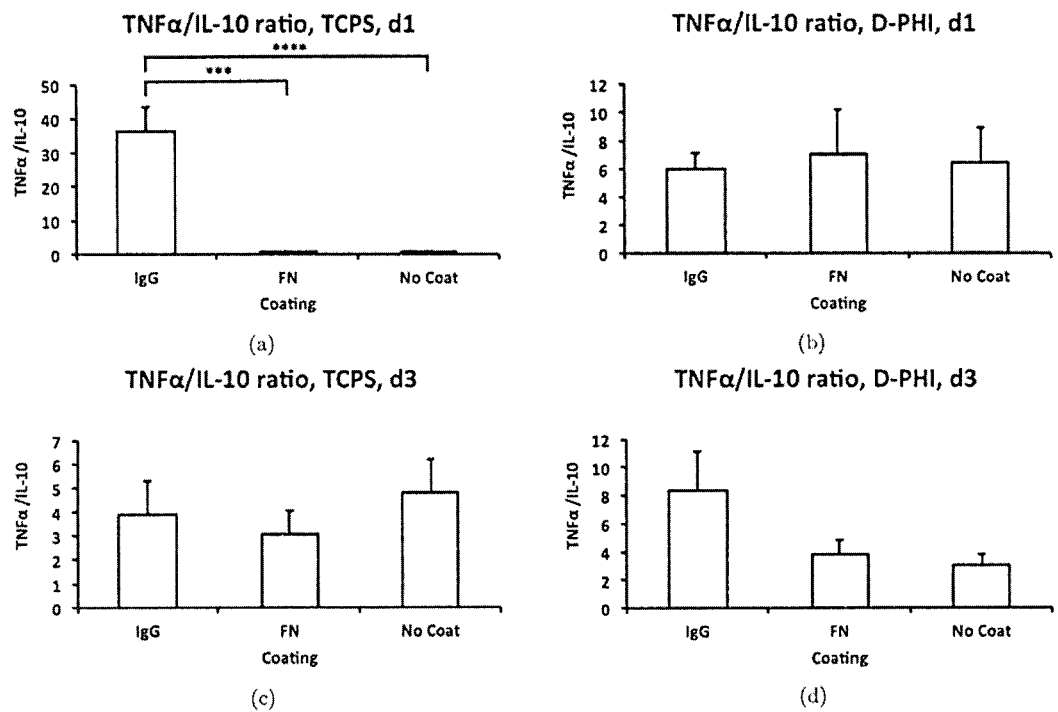

On TCPS at day 1, monocytes appeared to be very strongly activated by IgG (FIG. 9(a)), where the TNFα/IL-10 ratio was over 50 times greater on the IgG condition than the others, but the effect disappears at day 3 (FIG. 9 (c)). On D-PHI, IgG and FN were not different in activating monocytes at either day. There appeared to be a high dependence on type of serum used for the monocyte releasates for all other conditions. To compare the AHS vs. FBS vs. no serum conditions, monocytes on different adsorbed coatings but treated with the same serum were lumped together to form the three separate serum categories. From this larger dataset (n=24), the TNFα/IL-10 ratio was calculated for each sample, and averaged.

For both TCPS and D-PHI, monocytes cultured in 10% AHS saw a high ratio on day 1, indicating high activation, and then a drop on day 3, indicating a more anti-inflammatory state. This is a desirable outcome to have monocytes switch from an activated state after injury (for in vitro experiments, the injury is removing the cells from their natural in vivo environment) to a wound-healing state days later to begin the repair process. In contrast, cells cultured in 10% FBS increase their ratio by day 3, suggesting that the cells had become more inflammatory. This could be due to monocytes recognizing the xenoproteins in FBS as foreign, and thus shifting to a more-activated state the longer they are exposed to it. Monocytes cultured in FBS produced more total TNFα and IL-10 than monocytes in AHS, regardless of material or type of adsorbed protein. Foreign growth factors and cytokines in FBS could push monocytes into overdrive, causing them to upregulate all cytokine production.

5.4 Adsorbed Protein Quantification

TCPS, D-PHI (in PPL well), and PLGA (5 mm diameter disc on glass coverslip in TCPS well) were incubated with 100 µL human IgG at 200 µg/ml in RPMI for 24 hours at 37° C. overnight. IgG Fab exposure quantification and total adsorbed IgG quantification were performed as described in Examples 2.1 and 2.2, respectively.

Figure 10:
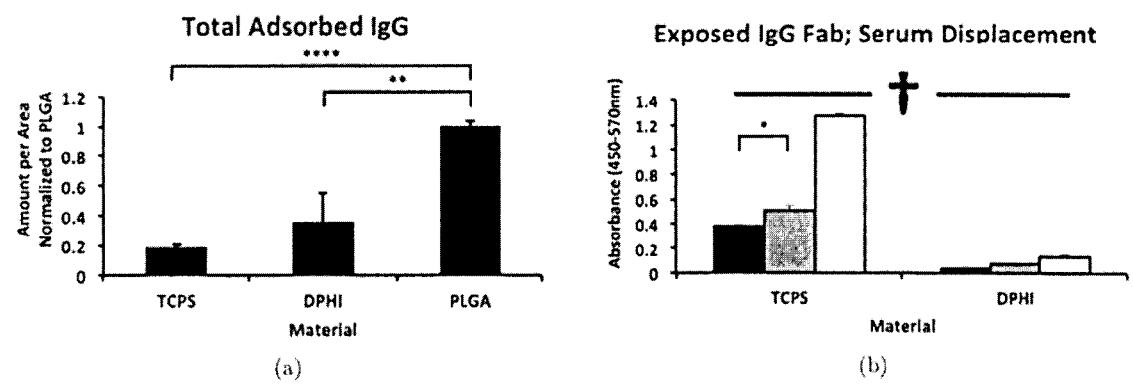

The cause of the high activating effect of adsorbed IgG was investigated. D-PHI adsorbed more IgG than TCPS but less than PLGA (0.18±0.02 and 0.35±0.20, respectively, normalized to PLGA; FIG. 10(a)). However, there was less exposed IgG Fab on D-PHI than on TCPS, as shown by an order of magnitude difference in the absorbance signals of the two (FIG. 10(b)).

Figure 11:
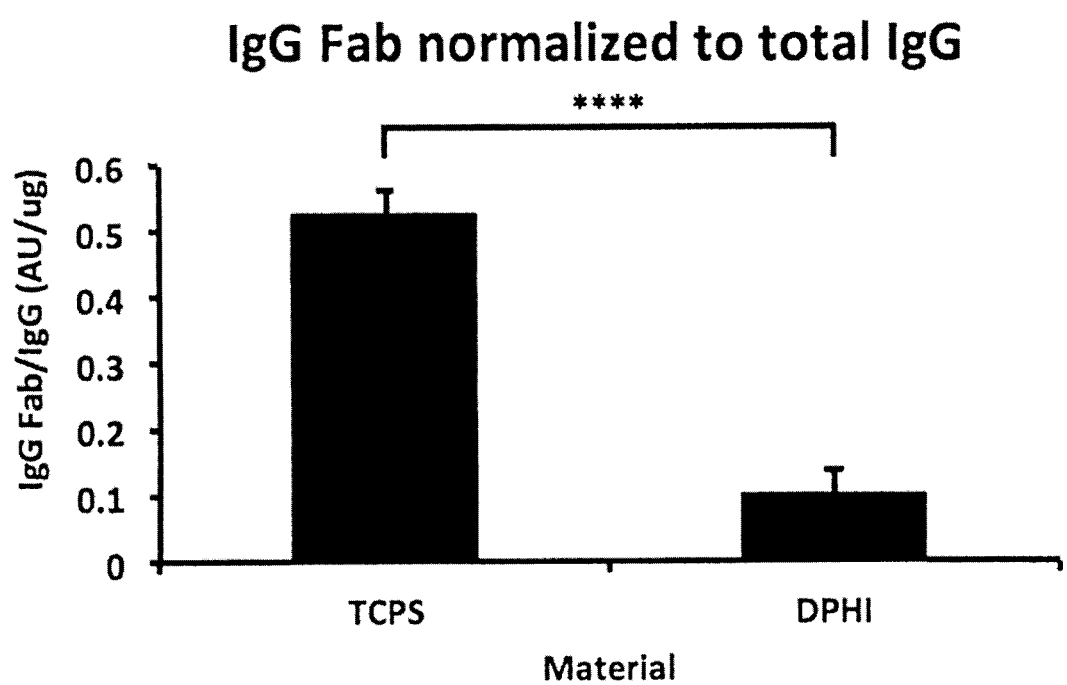

The amount of IgG Fab normalized to total IgG is shown in FIG. 11. There is more total IgG adsorbed to D-PHI, but less Fab region is exposed.

5.5 SEM Imaging

Figure 12:
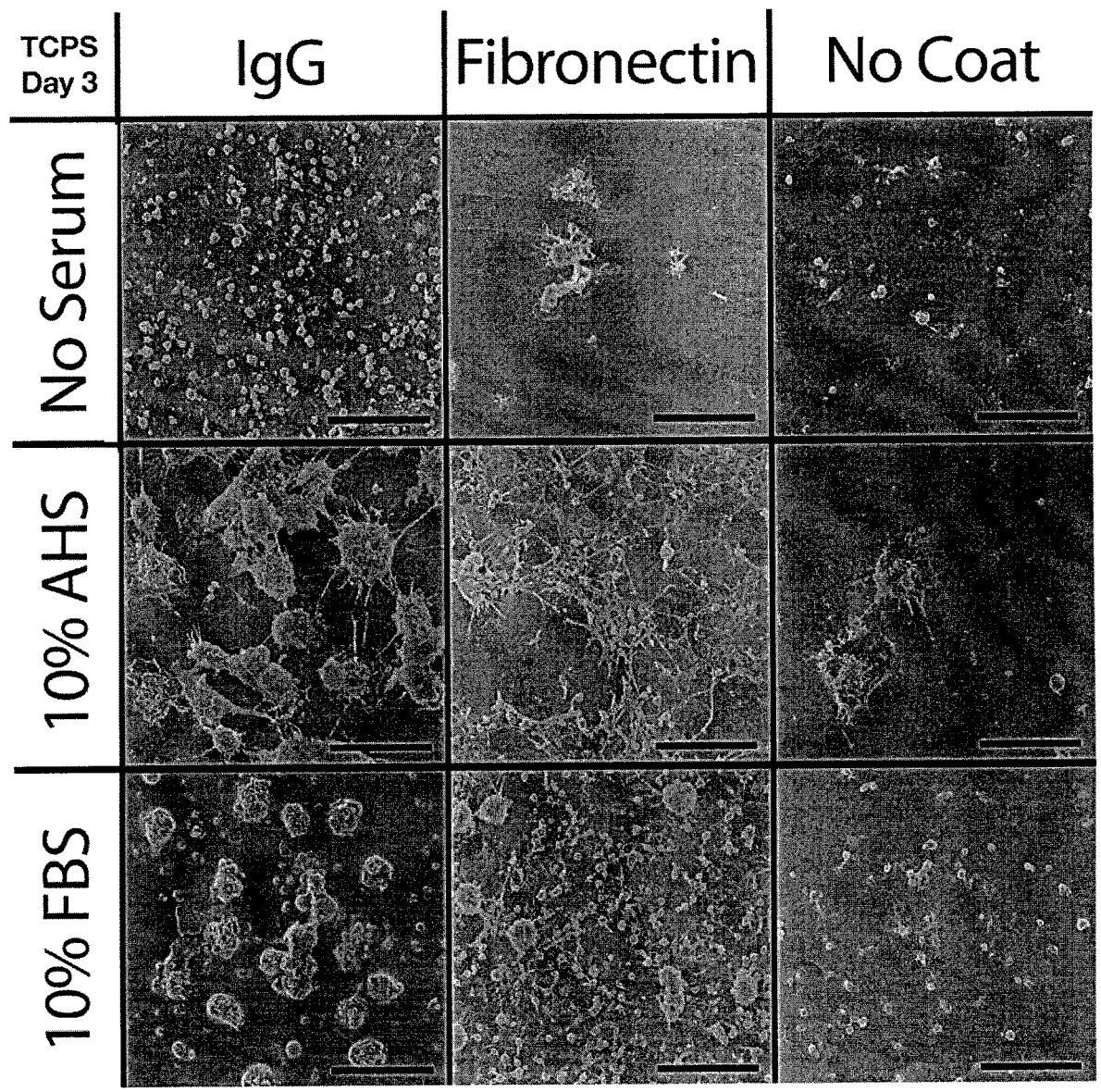
Figure 13:
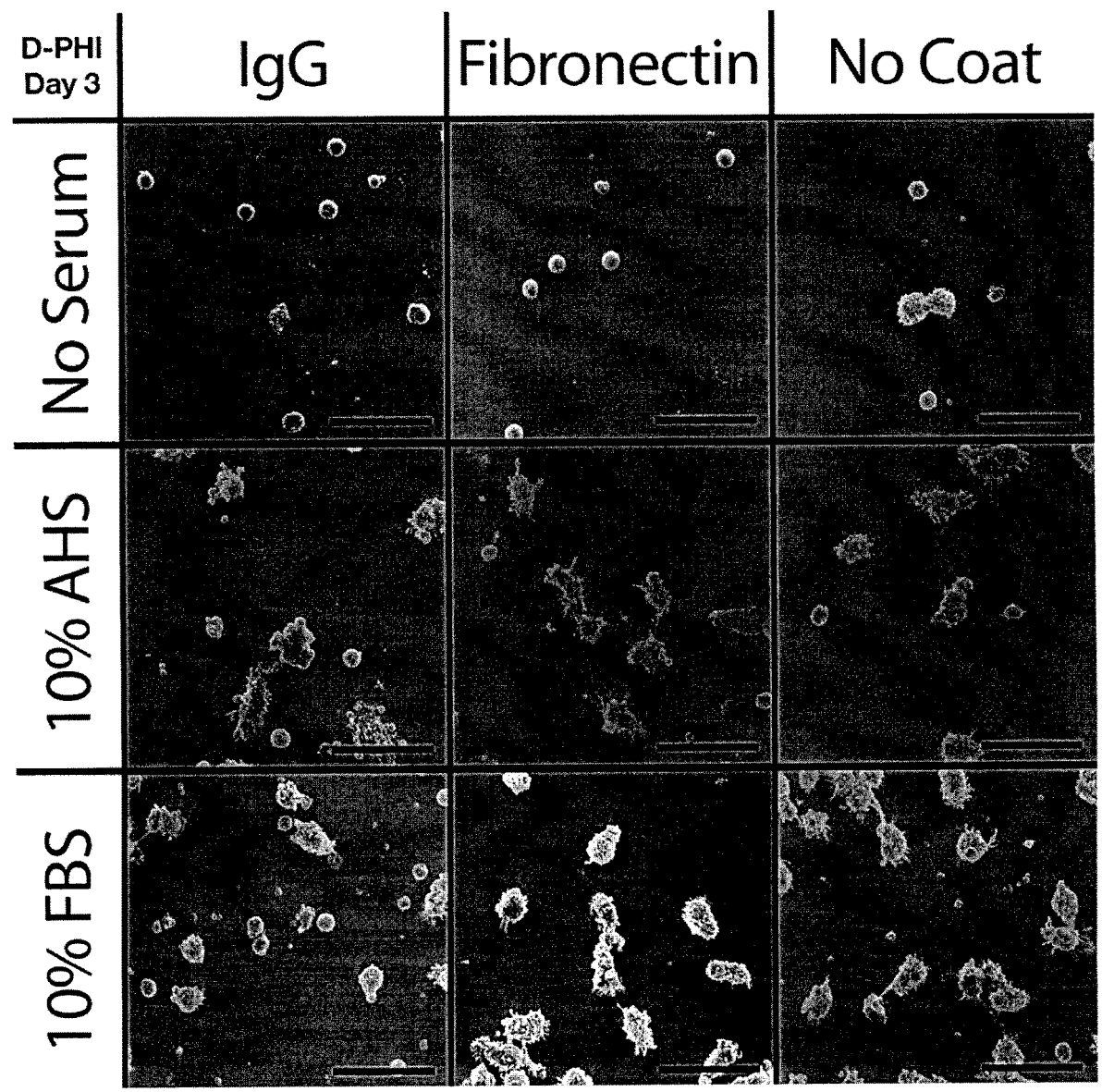

SEM analysis of monocyte-seeded surfaces was performed as described in Example 4.4. At day 1, monocytes had no observable difference between adsorbed proteins, materials, and serum type under SEM. At day 3, the differences were stark (FIGS. 12 and 13). On TCPS, cells cultured without serum behaved typically of serum-starved cells: they were small and sparse. On TCPS (FIG. 12), the cell response appeared to have both protein and material dependence. In 10% FBS on adsorbed IgG, the cells are much more enlarged than on the no serum condition. In the no coating condition, the cells appeared to be as small and sparse as cells cultured in no serum, even though they were cultured in 10% FBS. Cells seeded on IgG and cultured in AHS were more spindly than the rounded FBS cells. This is consistent with previous observations and has been speculated to be due to AHS having more recognizable soluble and adsorbed proteins to activate receptors and cause greater cytoplasmic extension [David Schmidt, Evan Joyce, and Weiyuan Kao. Fetal bovine serum xenoproteins modulate human monocyte adhesion and protein release on biomaterials in vitro. Acta biomaterialia, 7(2):51525, January 2011]].

On D-PHI, cells were much smaller and much less spread than on TCPS, regardless of culture serum or adsorbed proteins (FIG. 13), and within the D-PHI family, a very specific group showed the lowest cellular activation. Large and spread monocytes are indicative of a higher activated state [T Young, D Lin, and L Chen. Human monocyte adhesion and activation on crystalline polymers with different morphology and wettability in vitro. Journal of biomedical materials research, 50(4): 490-198, 2000; M. Benahmed, J Bouler, D Heymann, O Gan, and G Daculsi. Biodegradation of synthetic biphasic calcium phosphate by human monocytes in vitro: a morphological study. Biomaterials, 17(22): 2173-2178, 1996; 70, 71]. Thus, these observations suggest that D-PHI is a much less activating material than TCPS. The lack of dependence of monocyte activation on pre-adsorbed protein (IgG, FN, or no protein) and the type of serum suggests that D-PHI preferentially binds and exposes more non-activating regions of proteins to yield a lower inflammatory response than TCPS.

Example 6—Blocking Exposed Fab Prevents IgG-Induced Monocyte Activation 6.1 Preparation of D-PHI Films D-PHI-1:5:15 films were synthesized as described in Example 1.

6.2 Monocyte Isolation and Culture

Samples were prepared for cell culture and seeded with monocytes as described in Example 4.1. In addition, medium used to culture monocyte-seeded and IgG-coated D-PHI and TCPS surfaces was supplemented with 20 µg/ml anti-Fab specific IgG every 24 hr to block exposed Fab from interacting with adherent monocytes.

6.3 DNA Mass Quantification

DNA mass analysis of monocyte-seeded D-PHI and TCPS surfaces was performed as described in Example 4.2. Blocking exposed Fab on IgG-coated TCPS resulted in DNA levels at the same level of the non-coated TCPS control surface, further supporting the importance of Fab exposure in supporting IgG-mediated monocyte adhesion to this biomaterial surface. D-PHI was previously shown to support minimal IgG Fab exposure (Example 2). As a result, blocking exposed Fab had no effect on monocyte retention to IgG-coated D-PHI.

6.4 SEM

SEM analysis was performed as described in Example 4.4. Blocking exposed Fab on IgG-coated TCPS prevented IgG-induced monocyte spreading, with monocytes demonstrating a similar morphology to that observed for the non-coated control. Monocytes on IgG-coated and non-coated D-PHI maintained a round, non-spread morphology both with and without Fab blocking, demonstrating the attenuation of IgG-mediated monocyte spreading by D-PHI as opposed to TCPS, where exposed Fab supports enhanced monocyte activation.

Example 7—D-PHI Synthesis Using a Light-Cure System

These data demonstrate the feasibility of a light-cure system to cure D-PHI films.

7.1 D-PHI Film Synthesis

D-PHI films were synthesized by reacting a divinyl oligomer (DVO) with methacrylic acid (MAA, Sigma-Aldrich) and methyl methacrylate (MMA, Sigma) in a 1:5:15 molar ratio. Photopolymerization was initiated with camphorquinone and 2-(dimethylamino)ethyl methacrylate. The resulting mixture was pipetted into Teflon molds sealed with Mylar™ strips, and subsequently photopolymerized for 40 sec from each side (Sapphire plus, DenMat, Santa Maria, Calif., USA).

7.2 Gel Content Measurement

Gel content measurements were performed as described in section 3.5. Photopolymerized D-PHI films had a gel content of 98.8±0.7%, indicating a high degree of monomer conversion using the light-cure system.

Example 8—D-PHI Synthesis Using Different Hydrophobic Components

These data demonstrate the feasibility of producing D-PHI formulations with different hydrophobic chemistries.

8.1 D-PHI Film Synthesis

D-PHI films were synthesized by reacting DVO with MAA and a hydrophobic methacrylate in a 1:5:15 molar ratio. The hydrophobic methacrylate was either butyl methacrylate (BuMA, Sigma), hexyl methacrylate (HMA, Sigma), benzyl methacrylate (BzMa, Sigma), or 2,2,2-trifluoroethyl methacrylate (TFEMA, Sigma). Photopolymerization was initiated with camphorquinone and 2-(dimethylamino)ethyl methacrylate. The resulting mixture was pipetted into a 96-well polypropylene plate and subsequently photopolymerized for 3 min (Sapphire plus, DenMat, Santa Maria, Calif., USA).

8.2 Gel Content Measurement

Gel content measurements were performed as described in section 3.5. Photopolymerized D-PHI films had a gel content of >88%, indicating a high degree of monomer conversion using the light-cure system.

8.3 Adsorbed IgG Fab Quantification

Adsorbed IgG Fab quantification was performed as described in Example 2.1. The formulations containing BzMA and TFEMA had elevated Fab exposure compared to the 1:5:15 formulation with MMA. Otherwise, the other hydrophobic methacrylates had reduced Fab exposure comparable to the use of MMA (FIG. 15).

Example 9—D-PHI Synthesis Using Different Ratios of (b) to (c) and (a) to (b)+(c)

These data demonstrate the feasibility of producing D-PHI formulations with the following formulation characteristics:

high (b) to (c) ratio (10:1)
high (c) to (b) ratio (100:1)
high ratio of (a) to combined (b) and (c) (1:4)
low ratio of (a) to combined (b) and (c) (1:100)

9.1 D-PHI Film Synthesis

D-PHI films were synthesized by reacting DVO with MAA and MMA in ratios of 1:33:66 (low (a) to combined (b) and (c)), 1:55:5 (high (b) to (c)), 1:0.6:60 (high (c) to (b)), 1:3.33:0.66 (high (a) to combined (b) and (c)). Photopolymerization was initiated with camphorquinone and 2-(dimethylamino)ethyl methacrylate. The resulting mixture was pipetted into a 96-well polypropylene plate and subsequently photopolymerized for 3 min (Sapphire plus, DenMat, Santa Maria, Calif., USA).

9.2 Gel Content Measurement

Gel content measurements were performed as described in section 3.5. Photopolymerized D-PHI films had a gel content of >90%, indicating a high degree of monomer conversion using the light-cure system for all the different ratios tested.

9.3 Adsorbed IgG Fab Quantification

Adsorbed IgG Fab quantification was performed as described in Example 2.1. All the new formulations tested exhibited reduced Fab exposure compared to commercial TCPS, as well as other commercial materials such as polytetrafluoroethylene (PTFE), polycaprolactone (PCL), and commercial polyurethanes (Carbothane®, Tecoflex®). All formulations with a low ratio of (a) to combined (b) and (c) had low Fab exposure, regardless of the ratio of (b) to (c) within these formulations, while having a high ratio of (a) to combined (b) and (c) resulted in higher levels of Fab exposure, though still lower than most commercial materials (lower than TCPS, PCL, Carbothane, and PTFE, but the same as Tecoflex).

Example 10—Synthesis of a Monovinyl Oligomer (MVO) for Component (a)

These data demonstrate the feasibility of producing a monovinyl version of component (a) that can be used in combination with a divinyl version of component (a) in order to reduce polymer cross-link density and thus enable faster degradation rates. The MVO is used as part of the polar non-ionic component (a), such that combined DVO and MVO represent the total contribution of component (a). The presence of DVO with the use of MVO confers the cross-linking functionality of (a).

10.1 Monovinyl Oligomer Synthesis

A mixture of a monovinyl oligomer (MVO) and DVO was synthesized using LDI, polycarbonate (PCN), HEMA, and polyethylene glycol (PEG) in a 1.00:2.00:1.00:1.25 molar ratio under nitrogen. Briefly, PCN was dissolved in dimethylacetamide (DMAc). The temperature of the solution was brought to 45° C., after which LDI was added followed by dibutyltin dilaurate (catalyst). The temperature was maintained at 45° C. for 4 hr, after which HEMA was added. Following 2 hr at 40° C., PEG was added and the reaction was maintained for a further 16 hr at 40° C. The resulting polymer mixture was recovered by precipitation in a water/ether mixture.

10.2 $^1$H-NMR Characterization

The structure of the synthesized MVO was confirmed by $^1$H-NMR using a Varian Mercury 300 MHz spectrometer (University of Toronto). Samples were prepared in deuterated chloroform and peaks were reported relative to a tetramethylsilane reference peak. 1.4 (32H, $CH_2$—$CH_2$—C), 1.5 (4H, $CH_2$—$CH_2$—NH—COO), 1.68 (28H, $CH_2$—$CH_2$—OCO), 1.76 (4H, $CH_2$—CH—NH—COO), 1.95 (3H, $CH_3$—C=$CH_2$), 3.16 (4H, $CH_2$—NH—COO), 3.38 (3H, $CH_3$-0), 3.65 (24H, $CH_2$—$CH_2$—O), 3.75 (6H, $CH_3$—OCO), 4.12 (24H, $CH_2$—OCOO), 4.26 (2H, OOC—CH—NH—COO), 4.32 (12H, $CH_2$—OCO), 5.59 (2H, cis-$CH_2$=C($CH_3$)COO), 6.13 (2H, trans-$CH_2$=C($CH_3$)COO).

10.3 D-PHI Film Synthesis with an MVO as Part of Component (a)

D-PHI films were synthesized by reacting a mixture of MVO and DVO with MAA and MMA in a 1:5:15 molar ratio. Photopolymerization was initiated with camphorquinone and 2-(dimethylamino)ethyl methacrylate. The resulting mixture was pipetted into a 96-well polypropylene plate and subsequently photopolymerized for 3 min (Sapphire plus, DenMat, Santa Maria, Calif., USA).

10.4 Gel Content Measurement

Gel content measurements were performed as described in section 3.5.

Photopolymerized D-PHI films had a gel content of >90%, indicating a high degree of monomer conversion using the light-cure system for all the different ratios tested.

10.5 Adsorbed IgG Fab Quantification

Adsorbed IgG Fab quantification was performed as described in Example 2.1. The formulation containing PEG-MVO had reduced Fab exposure compared to commercial TCPS and comparable to the 1:5:15 formulation (FIG. 17).

Example 11—D-PHI Synthesis Using Components (a)+(b) or (a)+(c) Only

These data demonstrate the use of D-PHI formulations that contain only components (a) and (b) or (a) and (c) while maintaining low Fab exposure.

11.1 D-PHI Film Synthesis

D-PHI films were synthesized by reacting DVO with MAA in a 1:20 molar ratio or DVO and MMA in a 1:20 molar ratio. The resulting mixture was pipetted into a 96-well polypropylene plate and subsequently photopolymerized for 3 min (Sapphire plus, DenMat, Santa Maria, Calif., USA).

11.2 Adsorbed IgG Fab Quantification

Adsorbed IgG Fab quantification was performed as described in Example 2.1. DVO:MAA:MMA ratio of 1:0:20 was the same as 1:5:15, suggesting the presence of (b) is not necessary for reduced Fab exposure provided sufficient (c) is present. Furthermore, a ratio of 1:20:0 resulted in a lower Fab exposure than the 1:5:15 ratio, suggesting the presence of (c) is not required if sufficient (b) is present. All formulations were lower than commercial TCPS (FIG. 18).

Example 12—Coating an Object with D-PHI by Spray Coating

These data demonstrate the ability to coat an object, in this case a glass ceramic, with D-PHI polymer by spray coating.

12.1 D-PHI Film Synthesis

D-PHI films were synthesized by reacting DVO with MAA in a 1:20 molar ratio or DVO and MMA in a 1:20 molar ratio. The resulting mixture was spray-coated on a glass ceramic material and subsequently photopolymerized for 10 min (Sapphire plus, DenMat, Santa Maria, Calif., USA).

12.2 Contact Angle Measurements

Water contact angle measurements were performed for coated vs. non-coated areas of the glass ceramic material. Coated areas had a contact angle of 83±1, while non-coated areas had a contact angle of 52±2, indicating a successful coating of the polymer on the substrate. Data are the mean±s.d. n=3.

What is claimed is:

1. A synthetic biocompatible polymer material comprising the reaction product of:
   (a) at least one polar non-ionic macromer component;
   (b) at least one anionic component; and
   (c) at least one hydrophobic component;
   wherein the molar ratio of (b) to (c) is between 20:1 and 1:100; and
   wherein the maximum combined number of components (a), (b) and (c) in the polymer is 9; wherein the molar ratio of (a) to (b) plus (c) combined is at least 1:>20; and
   wherein the molar ratio of (a) to (b) plus (c) combined is such that the reaction product interacts with human IgG in a manner than yields a lower IgG Fab exposure, as determined by ELISA, as compared to the reaction product of (a), (b), and (c) having a molar ratio of (a) to (b) plus (c) combined of 1:20.

2. The biocompatible polymer material of claim 1, wherein the molar ratio of (b) to (c) is between 10:1 and 1:100.

3. The biocompatible polymer material of claim 2, wherein the molar ratio of (a) to (b) plus (c) combined is between 1:21 and 1:100.

4. The biocompatible polymer material of claim 1, wherein the molar ratio of (a) to (b) plus (c) combined is at least 1:21, at least 1:30, a least 1:40, at least 1:50, at least 1:60, at least 1:70, at least 1:80, or at least 1:100; or the molar ratio of (a) to (b) plus (c) combined is between 1:>20 and 1:100.

5. The biocompatible polymer material of claim 1, wherein the polymer material interacts with human IgG in a manner that yields an IgG Fab exposure as determined by ELISA of less than about 0.9, less than about 0.85, less than about 0.8, less than about 0.75, less than about 0.7, less than about 0.65, less than about 0.6, less than about 0.55, less than about 0.5, less than about 0.45, less than about 0.4, less than about 0.35, less than about 0.3, less than about 0.25, less than about 0.2 or less than about 0.15 of the value generated by a degradable polar hydrophobic ionic polyurethane, which has a monomer ratio of divinyl oligomer: methacrylic acid: methyl methacrylate of 1:1:7.

6. The biocompatible polymer material of claim 5, wherein the polymer material interacts with human IgG in a manner that yields an IgG Fab exposure as determined by ELISA of less than about 0.5 of the value generated by a degradable polar hydrophobic ionic polyurethane, which has a monomer ratio of divinyl oligomer: methacrylic acid: methyl methacrylate of 1:1:7.

7. The biocompatible polymer material of claim 1, wherein the molecular weight of each polar non-ionic macromer component of (a) is between about 400 and about 5000, about 500 and about 5000, about 1000 and about 5000, about 1000 and about 4000, about 1000 and 4500 or about 1500 and about 4500.

8. The biocompatible polymer material of claim 7, wherein the molecular weight of each polar non-ionic macromer component of (a) is between about 400 and about 5000.

9. The biocompatible polymer material of claim 1, wherein the molecular weight of each anionic component of (b) is between about 50 and about 1000.

10. The biocompatible polymer material of claim 1, wherein the molecular weight of each hydrophobic component of (c) is between about 50 and about 1000.

11. The biocompatible polymer material of claim 1, wherein the macromer is the reaction product of at least one isocyanate compound, at least one polyol terminated with hydroxyl or amine groups and at least one vinyl coupling agent.

12. The biocompatible polymer material of claim 11, wherein the macromer is the reaction product of poly(hexamethylene carbonate) diol, lysine diisocyanate and 2-hydroxyethyl methacrylate.

13. The biocompatible polymer material of claim 1, wherein the anionic component is selected from vinyl monomers with mono acid function; vinyl monomers with di-acids; and vinyl monomers with tri-acids.

14. The biocompatible polymer material of claim 13, wherein the anionic component is methacrylic acid, vinyl phosphoric acid, itaconic acid, maleic acid, tricarballylic acid or tricarboxylic acid.

15. The biocompatible polymer material of claim 1, wherein the anionic component is methacrylic acid.

16. The biocompatible polymer material of claim 1, wherein the hydrophobic component is an alkyl methacrylate, wherein the alkyl chain is linear or branched, saturated or unsaturated, and wherein the number of carbons is less than 12.

17. The biocompatible polymer material of claim 16, wherein the hydrophobic component is methyl methacrylate.

18. The biocompatible polymer material of claim 1, wherein a light curing system is used to polymerize the biocompatible polymer material.

19. The biocompatible polymer material of claim 18, wherein photopolymerization is initiated with camphorquinone and 2-(dimethylamino)ethyl methacrylate.

20. The biocompatible polymer material of claim 1 further comprising one or more additives in admixture selected from antioxidants, fillers, cross-linkers, plasticizers, nucleating agents, or pigments.

21. The biocompatible polymer material of claim 1 in admixture with a therapeutic agent.

22. The biocompatible polymer material of claim 1, wherein the material is in the form of a formed object, a coating, a film, a foam, a gel, or a particulate.

23. A method of decreasing IgG Fab exposure in a synthetic biocompatible polymer material exposed to IgG, the polymer material comprising the reaction product of:
    (a) at least one polar non-ionic macromer component;
    (b) at least one anionic component; and
    (c) at least one hydrophobic component;
    wherein the molar ratio of (b) to (c) is between 20:1 and 1:100; and
    wherein the maximum combined number of components (a), (b) and (c) in the polymer is 9; and wherein the molar ratio of (a) to (b) plus (c) combined is at least 1:>20;
    the method comprising increasing the molar ratio of (a) to (b) plus (c) combined to at least 1:>20 such that the polymer material interacts with human IgG in a manner that yields a lower IgG Fab exposure, as determined by ELISA, as compared to the reaction product of (a), (b) and (c) having a molar ratio of (a) to (b) plus (c) combined of 1:20.

* * * * *